(12) United States Patent
Coe et al.

(10) Patent No.: US 8,187,162 B2
(45) Date of Patent: May 29, 2012

(54) REORIENTATION PORT

(75) Inventors: Jonathan A. Coe, Cincinnati, OH (US);
Christine Chen, Cincinnati, OH (US);
Juan S. Ezolino, Weston, FL (US);
Kevin D. Felder, Cincinnati, OH (US);
Eric Thompson, Pleasant Plain, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1119 days.

(21) Appl. No.: 12/043,541

(22) Filed: Mar. 6, 2008

(65) Prior Publication Data
US 2009/0228028 A1    Sep. 10, 2009

(51) Int. Cl.
*A61F 5/37* (2006.01)
(52) U.S. Cl. .................. 600/33; 128/899; 604/288.01
(58) Field of Classification Search ................ 600/37; 604/523, 533, 540, 890.1, 891.1, 288.01, 604/288.02, 288.04; 606/157; 128/899
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |

(Continued)

FOREIGN PATENT DOCUMENTS

CA    1059035    7/1979

(Continued)

OTHER PUBLICATIONS

European Search Report, Application No. 09250629.4, Mailed Jun. 10, 2009.

(Continued)

*Primary Examiner* — Samuel Gilbert
*Assistant Examiner* — Joshua D Lannu
(74) *Attorney, Agent, or Firm* — Nutter McClennen & Fish LLP

(57) ABSTRACT

Various methods and devices are provided for reorienting an implantable port. In one embodiment, an implantable port is provided and includes a base adapted to be anchored to tissue, and a housing pivotally mounted on the base and having a septum formed therein and adapted to receive fluid and to provide access to a fluid reservoir formed within the housing. In an exemplary embodiment, the housing can be pivotally mounted to the base using a ball and socket joint. For example, at least one of a distal surface of the housing and a proximal surface of the base is convex, and the other one of the distal surface of the housing and the proximal surface of the base is concave.

10 Claims, 8 Drawing Sheets

U.S. PATENT DOCUMENTS

| | | | |
|---|---|---|---|
| 689,758 A | 12/1901 | Shaw | |
| 724,913 A | 4/1903 | Montgomery | |
| 899,477 A | 9/1908 | Williams | |
| 926,197 A | 6/1909 | Kim | |
| 953,875 A | 4/1910 | Waring | |
| 991,192 A | 5/1911 | Batttenfeld | |
| 1,087,988 A | 2/1914 | Sheldon | |
| 1,210,701 A | 1/1917 | Ryden | |
| 1,219,296 A | 3/1917 | Hahn | |
| 1,224,355 A | 5/1917 | Brown | |
| 1,263,914 A | 4/1918 | Martin | |
| 1,310,290 A | 7/1919 | Piechowicz | |
| 1,384,873 A | 7/1921 | Strickland | |
| 1,421,507 A | 7/1922 | Lindberg | |
| 1,551,525 A | 8/1925 | Hamer | |
| 1,560,973 A | 11/1925 | Cheron | |
| 1,620,633 A | 3/1927 | Colvin | |
| 1,623,403 A | 4/1927 | Friel | |
| 1,689,085 A | 10/1928 | Russell et al. | |
| 1,764,071 A | 6/1930 | Foulke | |
| 1,782,704 A | 11/1930 | Woodruff | |
| 1,807,107 A | 5/1931 | Sternberch | |
| 1,865,446 A | 7/1932 | Sears | |
| 1,882,338 A | 10/1932 | Reed et al. | |
| 1,924,781 A | 8/1933 | Gaiser | |
| 2,027,875 A | 1/1936 | Odend'hal | |
| 2,063,430 A | 12/1936 | Graser | |
| 2,099,160 A | 11/1937 | Charch | |
| 2,105,127 A | 1/1938 | Petrone | |
| 2,106,192 A | 1/1938 | Saville | |
| 2,143,429 A | 1/1939 | Auble | |
| 2,166,603 A | 7/1939 | Menzer | |
| 2,168,427 A | 8/1939 | McConkey | |
| 2,174,525 A | 10/1939 | Padernal | |
| 2,177,564 A | 10/1939 | Havill | |
| 2,178,463 A | 10/1939 | Bahnson | |
| 2,180,599 A | 11/1939 | Menasco | |
| 2,203,460 A | 6/1940 | Fieber | |
| 2,206,038 A | 7/1940 | Lang Ford | |
| 2,216,374 A | 10/1940 | Martin | |
| 2,223,699 A | 12/1940 | Norgren | |
| 2,225,145 A | 12/1940 | Baumbach | |
| 2,225,880 A | 12/1940 | Montelius | |
| 2,261,060 A | 10/1941 | Giesler | |
| 2,261,355 A | 11/1941 | Flynn | |
| 2,295,539 A | 9/1942 | Beach | |
| 2,303,108 A | 11/1942 | Blackburn | |
| 2,303,502 A | 12/1942 | Rous | |
| 2,318,819 A | 5/1943 | Verson | |
| 2,327,407 A | 8/1943 | Edyvean | |
| 2,327,615 A | 8/1943 | Ankarlo | |
| 2,354,571 A | 7/1944 | Blain | |
| 2,426,392 A | 8/1947 | Fennema | |
| 2,426,817 A | 9/1947 | Charlton et al. | |
| 2,440,260 A | 4/1948 | Gall | |
| 2,442,573 A | 6/1948 | Stafford | |
| 2,453,217 A | 11/1948 | Gregg et al. | |
| 2,455,859 A | 12/1948 | Foley | |
| 2,477,922 A | 8/1949 | Emery et al. | |
| 2,478,876 A | 8/1949 | Nelson | |
| 2,482,392 A | 9/1949 | Whitaker | |
| 2,494,881 A | 1/1950 | Kost | |
| 2,509,210 A | 5/1950 | Clark | |
| 2,509,673 A | 5/1950 | Church | |
| 2,511,765 A | 6/1950 | Bradbury | |
| 2,520,056 A | 8/1950 | Pozun | |
| 2,521,976 A | 9/1950 | Hays | |
| 2,533,924 A | 12/1950 | Foley | |
| 2,538,259 A | 1/1951 | Merriman | |
| 2,581,479 A | 1/1952 | Grashman | |
| 2,600,324 A | 6/1952 | Rappaport | |
| 2,606,003 A | 8/1952 | McNeill | |
| 2,615,940 A | 10/1952 | Williams | |
| 2,632,447 A | 3/1953 | Dobes | |
| 2,639,342 A | 5/1953 | Cope | |
| 2,640,119 A | 5/1953 | Bradford, Jr. | |
| 2,641,742 A | 6/1953 | Wolfe | |
| 2,651,304 A | 9/1953 | Browner | |
| 2,665,577 A | 1/1954 | Sanowskis | |
| 2,673,999 A | 4/1954 | Shey | |
| 2,676,609 A | 4/1954 | Pfarrer | |
| 2,684,118 A | 7/1954 | Osmun | |
| 2,689,611 A | 9/1954 | Martinson | |
| 2,697,435 A | 12/1954 | Ray | |
| 2,723,323 A | 11/1955 | Niemi | |
| 2,734,992 A | 2/1956 | Elliot et al. | |
| 2,740,007 A | 3/1956 | Amelang | |
| 2,740,853 A | 4/1956 | Hatman, Jr. | |
| 2,742,323 A | 4/1956 | Shey | |
| 2,747,332 A | 5/1956 | Morehouse | |
| 2,753,876 A | 7/1956 | Kurt | |
| 2,756,883 A | 7/1956 | Schreck | |
| 2,756,983 A | 7/1956 | Furcini | |
| 2,761,603 A | 9/1956 | Fairchild | |
| 2,773,312 A | 12/1956 | Peck | |
| 2,783,728 A | 3/1957 | Hoffmann | |
| 2,787,875 A | 4/1957 | Johnson | |
| 2,793,379 A | 5/1957 | Moore | |
| 2,795,460 A | 6/1957 | Bletcher | |
| 2,804,514 A | 8/1957 | Peters | |
| 2,822,113 A | 2/1958 | Joiner, Jr. | |
| 2,831,478 A | 4/1958 | Uddenberg et al. | |
| 2,864,393 A | 12/1958 | Drake | |
| 2,865,541 A | 12/1958 | Hicks | |
| 2,870,024 A | 1/1959 | Martin | |
| 2,883,995 A | 4/1959 | Bialous et al. | |
| 2,886,355 A | 5/1959 | Wurzel | |
| 2,895,215 A | 7/1959 | Neher et al. | |
| 2,899,493 A | 8/1959 | Levine | |
| 2,902,861 A | 9/1959 | Frost et al. | |
| 2,923,531 A | 2/1960 | Bauer et al. | |
| 2,924,263 A | 2/1960 | Landis | |
| 2,924,432 A | 2/1960 | Arps et al. | |
| 2,930,170 A | 3/1960 | Holsman et al. | |
| 2,938,592 A | 5/1960 | Charske et al. | |
| 2,941,338 A | 6/1960 | Santschi | |
| 2,943,682 A | 7/1960 | Ingram, Jr. et al. | |
| 2,958,781 A | 11/1960 | Marchal et al. | |
| 2,961,479 A | 11/1960 | Bertling | |
| 2,976,355 A | 3/1961 | Levine | |
| 2,976,686 A | 3/1961 | Stelzer | |
| 2,977,876 A | 4/1961 | Meyers | |
| 2,986,715 A | 5/1961 | Church et al. | |
| 2,989,019 A | 6/1961 | Van Sciver, II | |
| 3,010,692 A | 11/1961 | Jentoft | |
| 3,013,234 A | 12/1961 | Bourns | |
| 3,018,791 A | 1/1962 | Knox | |
| 3,034,356 A | 5/1962 | Bieganski | |
| 3,040,800 A | 6/1962 | Hartley | |
| 3,054,618 A | 9/1962 | Abrams et al. | |
| 3,060,262 A | 10/1962 | Hoer | |
| 3,070,373 A | 12/1962 | Mathews et al. | |
| 3,082,414 A | 3/1963 | Papaminas | |
| 3,085,577 A | 4/1963 | Berman et al. | |
| 3,096,410 A | 7/1963 | Anderson | |
| 3,099,262 A | 7/1963 | Bigliano | |
| 3,125,028 A | 3/1964 | Rohde | |
| 3,126,029 A | 3/1964 | Englesson | |
| 3,129,072 A | 4/1964 | Cook et al. | |
| 3,135,914 A | 6/1964 | Callan et al. | |
| 3,144,017 A | 8/1964 | Muth | |
| 3,151,258 A | 9/1964 | Sonderegger et al. | |
| 3,153,460 A | 10/1964 | Raskin | |
| 3,161,051 A | 12/1964 | Perry, Jr. | |
| 3,167,044 A | 1/1965 | Henrickson | |
| 3,171,549 A | 3/1965 | Orloff | |
| 3,172,700 A | 3/1965 | Haas | |
| 3,173,269 A | 3/1965 | Imbertson | |
| 3,182,494 A | 5/1965 | Beatty et al. | |
| 3,187,181 A | 6/1965 | Keller | |
| 3,187,745 A | 6/1965 | Baum et al. | |
| 3,190,388 A | 6/1965 | Moser et al. | |
| 3,205,547 A | 9/1965 | Riekse | |
| 3,208,255 A | 9/1965 | Burk | |
| 3,209,570 A | 10/1965 | Hills | |
| 3,221,468 A | 12/1965 | Casey | |
| 3,228,703 A | 1/1966 | Wilson | |

| | | | | | |
|---|---|---|---|---|---|
| 3,229,684 A | 1/1966 | Nagumo et al. | 3,505,808 A | 4/1970 | Eschle |
| 3,236,088 A | 2/1966 | Moller | 3,509,754 A | 5/1970 | Massingill et al. |
| 3,238,624 A | 3/1966 | McCabe | 3,512,517 A | 5/1970 | Kadish et al. |
| 3,240,510 A | 3/1966 | Spouge | 3,514,919 A | 6/1970 | Ashton et al. |
| 3,245,642 A | 4/1966 | Dicke | 3,516,220 A | 6/1970 | Buford et al. |
| 3,255,568 A | 6/1966 | Martin et al. | 3,517,553 A | 6/1970 | Williams et al. |
| 3,260,091 A | 7/1966 | Shaw, Jr. | 3,527,226 A | 9/1970 | Hakin et al. |
| 3,265,822 A | 8/1966 | Moulten | 3,529,908 A | 9/1970 | Smith |
| 3,266,487 A | 8/1966 | Watkins et al. | 3,530,449 A | 9/1970 | Anderson |
| 3,273,447 A | 9/1966 | Frank | 3,533,403 A | 10/1970 | Woodson |
| 3,283,352 A | 11/1966 | Yow-Jiun Hu | 3,534,728 A | 10/1970 | Barrows |
| 3,290,919 A | 12/1966 | Malinak et al. | 3,534,872 A | 10/1970 | Roth et al. |
| 3,292,493 A | 12/1966 | Franklin | 3,535,914 A | 10/1970 | Veith et al. |
| 3,292,888 A | 12/1966 | Fischer | 3,539,009 A | 11/1970 | Kudlaty |
| 3,294,988 A | 12/1966 | Packard | 3,543,744 A | 12/1970 | LePar |
| 3,299,603 A | 1/1967 | Shaw | 3,545,275 A | 12/1970 | Harrison et al. |
| 3,299,882 A | 1/1967 | Masino | 3,550,583 A | 12/1970 | Chiku |
| 3,301,514 A | 1/1967 | Sugaya | 3,550,847 A | 12/1970 | Scott |
| 3,302,457 A | 2/1967 | Mayes | 3,563,094 A | 2/1971 | Rieschel |
| 3,306,384 A | 2/1967 | Ross | 3,563,245 A | 2/1971 | McLean et al. |
| 3,313,314 A | 4/1967 | Burke et al. | 3,566,083 A | 2/1971 | McMillin |
| 3,316,935 A | 5/1967 | Kaiser et al. | 3,566,875 A | 3/1971 | Stoehr |
| 3,320,750 A | 5/1967 | Haise et al. | 3,568,367 A | 3/1971 | Myers |
| 3,321,035 A | 5/1967 | Tarpley | 3,568,636 A | 3/1971 | Lockwood |
| 3,332,788 A | 7/1967 | Barnby | 3,576,554 A | 4/1971 | Temps, Jr. et al. |
| 3,334,510 A | 8/1967 | Hallesy | 3,580,082 A | 5/1971 | Strack |
| 3,339,401 A | 9/1967 | Peters | 3,581,402 A | 6/1971 | London et al. |
| 3,340,868 A | 9/1967 | Darling | 3,583,387 A | 6/1971 | Garner et al. |
| 3,347,162 A | 10/1967 | Braznell | 3,587,204 A | 6/1971 | George |
| 3,350,944 A | 11/1967 | DE Michele | 3,590,809 A | 7/1971 | London |
| 3,353,364 A | 11/1967 | Blanding et al. | 3,590,818 A | 7/1971 | Lemole |
| 3,353,481 A | 11/1967 | Antonucci | 3,590,992 A | 7/1971 | Soderstrom et al. |
| 3,356,334 A | 12/1967 | Scaramucci | 3,592,183 A | 7/1971 | Watkins et al. |
| 3,356,510 A | 12/1967 | Barnby | 3,594,519 A | 7/1971 | Schmidlin |
| 3,357,218 A | 12/1967 | Mitchell | 3,602,885 A | 8/1971 | Grajeda |
| 3,357,461 A | 12/1967 | Friendship | 3,610,016 A | 10/1971 | Bultman |
| 3,359,741 A | 12/1967 | Nelson | 3,610,851 A | 10/1971 | Krupski |
| 3,361,300 A | 1/1968 | Kaplan | 3,611,811 A | 10/1971 | Lissau |
| 3,364,929 A | 1/1968 | Ide et al. | 3,614,926 A | 10/1971 | Brechtel |
| 3,365,684 A | 1/1968 | Stemke | 3,614,955 A | 10/1971 | Mirowski et al. |
| 3,378,456 A | 4/1968 | Roberts | 3,619,742 A | 11/1971 | Rud, Jr. |
| 3,380,445 A | 4/1968 | Frasier | 3,623,371 A | 11/1971 | Jullien-Davin |
| 3,380,649 A | 4/1968 | Roberts | 3,624,854 A | 12/1971 | Strong |
| 3,385,022 A | 5/1968 | Anderson | 3,630,242 A | 12/1971 | Schieser et al. |
| 3,389,355 A | 6/1968 | Schroeder, Jr. | 3,631,847 A | 1/1972 | Hobbs, II |
| 3,393,612 A | 7/1968 | Gorgens et al. | 3,633,881 A | 1/1972 | Yurdin |
| 3,396,561 A | 8/1968 | Day | 3,635,061 A | 1/1972 | Rydell |
| 3,399,667 A | 9/1968 | Nishimoto et al. | 3,635,074 A | 1/1972 | Moos et al. |
| 3,400,734 A | 9/1968 | Rosenberg | 3,638,496 A | 2/1972 | King |
| 3,403,237 A | 9/1968 | Wysong | 3,644,883 A | 2/1972 | Borman et al. |
| 3,409,924 A | 11/1968 | Slama | 3,648,687 A | 3/1972 | Ramsey, III |
| 3,411,347 A | 11/1968 | Wirth et al. | 3,651,289 A | 3/1972 | Nagashima et al. |
| 3,417,476 A | 12/1968 | Martens | 3,651,405 A | 3/1972 | Whitney et al. |
| 3,420,325 A | 1/1969 | McAlister et al. | 3,653,671 A | 4/1972 | Shipes |
| 3,422,324 A | 1/1969 | Webb | 3,659,615 A | 5/1972 | Enger |
| 3,426,165 A | 2/1969 | Beaman | 3,677,685 A | 7/1972 | Aoki et al. |
| 3,438,391 A | 4/1969 | Yocum | 3,686,958 A | 8/1972 | Porter et al. |
| 3,443,608 A | 5/1969 | Copping et al. | 3,688,568 A | 9/1972 | Karper et al. |
| 3,445,335 A | 5/1969 | Gluntz | 3,701,392 A | 10/1972 | Wirth et al. |
| 3,447,281 A | 6/1969 | Bufford et al. | 3,702,677 A | 11/1972 | Heffington |
| 3,450,153 A | 6/1969 | Hildebrandt et al. | 3,703,099 A | 11/1972 | Rouse et al. |
| 3,453,546 A | 7/1969 | Fryer | 3,712,138 A | 1/1973 | Alinari et al. |
| 3,453,848 A | 7/1969 | Williamson | 3,713,124 A | 1/1973 | Durland et al. |
| 3,456,134 A | 7/1969 | Ko | 3,719,524 A | 3/1973 | Ripley et al. |
| 3,457,909 A | 7/1969 | Laird | 3,721,412 A | 3/1973 | Kindorf |
| 3,460,557 A | 8/1969 | Gallant | 3,723,247 A | 3/1973 | Leine et al. |
| 3,463,338 A | 8/1969 | Schneider | 3,724,000 A | 4/1973 | Eakman |
| 3,469,818 A | 9/1969 | Cowan | 3,727,463 A | 4/1973 | Intraub |
| 3,470,725 A | 10/1969 | Brown et al. | 3,727,616 A | 4/1973 | Lenzkes |
| 3,472,230 A | 10/1969 | Fogarty | 3,730,174 A | 5/1973 | Madison |
| 3,478,344 A | 11/1969 | Schwitzgebel et al. | 3,730,560 A | 5/1973 | Abildgaard et al. |
| 3,482,449 A | 12/1969 | Werner | 3,731,679 A | 5/1973 | Wilhelmson et al. |
| 3,482,816 A | 12/1969 | Arnold | 3,731,681 A | 5/1973 | Blackshear et al. |
| 3,487,959 A | 1/1970 | Pearne et al. | 3,732,731 A | 5/1973 | Fussell, Jr. |
| 3,491,842 A | 1/1970 | Delacour et al. | 3,735,040 A | 5/1973 | Punt et al. |
| 3,492,638 A | 1/1970 | Lane | 3,736,930 A | 6/1973 | Georgi |
| 3,502,829 A | 3/1970 | Reynolds | 3,738,356 A | 6/1973 | Workman |
| 3,503,116 A | 3/1970 | Strack | 3,740,921 A | 6/1973 | Meyer et al. |
| 3,504,664 A | 4/1970 | Haddad | 3,746,111 A | 7/1973 | Berthiaume et al. |

| | | | | | |
|---|---|---|---|---|---|
| 3,748,678 A | 7/1973 | Ballou | 3,921,682 A | 11/1975 | McGahey et al. |
| 3,749,098 A | 7/1973 | De Bennetot et al. | 3,922,951 A | 12/1975 | Linsinger et al. |
| 3,749,422 A | 7/1973 | Abildgaard et al. | 3,923,060 A | 12/1975 | Ellinwood, Jr. |
| 3,749,423 A | 7/1973 | Abildgaard et al. | 3,924,635 A | 12/1975 | Hakim et al. |
| 3,750,194 A | 8/1973 | Summers | 3,928,980 A | 12/1975 | Ganzinotti et al. |
| 3,757,770 A | 9/1973 | Brayshaw et al. | 3,929,175 A | 12/1975 | Coone |
| 3,759,095 A | 9/1973 | Short, Jr. et al. | 3,930,682 A | 1/1976 | Booth |
| 3,760,638 A | 9/1973 | Lawson et al. | 3,930,852 A | 1/1976 | Tanaka et al. |
| 3,763,960 A | 10/1973 | John et al. | 3,936,028 A | 2/1976 | Norton et al. |
| 3,765,142 A | 10/1973 | Lindquist et al. | 3,940,122 A | 2/1976 | Janzen |
| 3,765,494 A | 10/1973 | Kielman, Jr. | 3,940,630 A | 2/1976 | Bergonz |
| 3,769,156 A | 10/1973 | Brecy et al. | 3,942,299 A | 3/1976 | Bory et al. |
| 3,769,830 A | 11/1973 | Porter et al. | 3,942,382 A | 3/1976 | Hok et al. |
| 3,774,243 A | 11/1973 | Ng et al. | 3,942,516 A | 3/1976 | Glynn et al. |
| 3,776,333 A | 12/1973 | Mathauser | 3,942,536 A | 3/1976 | Mirowski et al. |
| 3,778,051 A | 12/1973 | Allen et al. | 3,943,915 A | 3/1976 | Severson |
| 3,780,578 A | 12/1973 | Sellman et al. | 3,945,704 A | 3/1976 | Kraus et al. |
| 3,781,902 A | 12/1973 | Shim et al. | 3,946,613 A | 3/1976 | Silver |
| 3,783,585 A | 1/1974 | Hoyland et al. | 3,946,615 A | 3/1976 | Hluchan |
| 3,789,667 A | 2/1974 | Porter et al. | 3,946,724 A | 3/1976 | La Balme et al. |
| 3,796,095 A | 3/1974 | Fussell, Jr. | 3,948,141 A | 4/1976 | Shinjo et al. |
| 3,807,219 A | 4/1974 | Wallskog | 3,949,388 A | 4/1976 | Fuller |
| 3,811,429 A | 5/1974 | Fletcher et al. | 3,953,289 A | 4/1976 | Costes et al. |
| 3,815,722 A | 6/1974 | Sessoms | 3,954,271 A | 5/1976 | Tredway, Sr. |
| 3,818,765 A | 6/1974 | Eriksen et al. | 3,958,558 A | 5/1976 | Dunphy et al. |
| 3,820,400 A | 6/1974 | Russo | 3,961,425 A | 6/1976 | Swanson et al. |
| 3,820,795 A | 6/1974 | Taylor | 3,961,646 A | 6/1976 | Schon et al. |
| 3,823,610 A | 7/1974 | Fussell, Jr. | 3,962,895 A | 6/1976 | Rydell et al. |
| 3,825,065 A | 7/1974 | Lloyd et al. | 3,962,921 A | 6/1976 | Lips |
| 3,825,963 A | 7/1974 | Abildgaard et al. | 3,963,019 A | 6/1976 | Quandt |
| 3,825,964 A | 7/1974 | Groswith, III et al. | 3,964,485 A | 6/1976 | Neumeier |
| 3,828,672 A | 8/1974 | Gazzola et al. | 3,964,770 A | 6/1976 | Abildgaard et al. |
| 3,828,766 A | 8/1974 | Krasnow | 3,967,737 A | 7/1976 | Peralta et al. |
| 3,831,588 A | 8/1974 | Rindner | 3,968,473 A | 7/1976 | Patton et al. |
| 3,831,942 A | 8/1974 | Del Mar | 3,968,694 A | 7/1976 | Clark |
| 3,833,238 A | 9/1974 | Liard et al. | 3,972,320 A | 8/1976 | Kalman |
| 3,834,167 A | 9/1974 | Tabor | 3,973,753 A | 8/1976 | Wheeler |
| 3,834,739 A | 9/1974 | Abildgaard et al. | 3,973,858 A | 8/1976 | Poisson et al. |
| 3,835,523 A | 9/1974 | Stansfield et al. | 3,974,655 A | 8/1976 | Halpern et al. |
| 3,839,708 A | 10/1974 | Bredesen et al. | 3,974,865 A | 8/1976 | Fenton et al. |
| 3,842,483 A | 10/1974 | Cramer | 3,977,391 A | 8/1976 | Fleischmann |
| 3,842,668 A | 10/1974 | Lippke et al. | 3,980,871 A | 9/1976 | Lindstrom et al. |
| 3,845,664 A | 11/1974 | Perry, Jr. | 3,982,571 A | 9/1976 | Fenton et al. |
| 3,845,751 A | 11/1974 | Runstetler | 3,983,948 A | 10/1976 | Jeter |
| 3,845,757 A | 11/1974 | Weyer | 3,985,133 A | 10/1976 | Jenkins et al. |
| 3,847,434 A | 11/1974 | Weman et al. | 3,987,860 A | 10/1976 | Jabsen |
| 3,850,208 A | 11/1974 | Hamilton | 3,989,005 A | 11/1976 | Bowler, Jr. et al. |
| 3,853,117 A | 12/1974 | Murr | 3,991,749 A | 11/1976 | Zent |
| 3,854,469 A | 12/1974 | Giori et al. | 3,992,948 A | 11/1976 | D'Antonio et al. |
| 3,855,902 A | 12/1974 | Kirst et al. | 3,993,149 A | 11/1976 | Harvey |
| 3,857,399 A | 12/1974 | Zacouto et al. | 3,996,927 A | 12/1976 | Frank |
| 3,857,452 A | 12/1974 | Hartman | 3,996,962 A | 12/1976 | Sutherland |
| 3,857,745 A | 12/1974 | Grausch et al. | 4,003,141 A | 1/1977 | Le Roy |
| 3,858,581 A | 1/1975 | Kamen | 4,005,282 A | 1/1977 | Jennings |
| 3,863,622 A | 2/1975 | Buuck | 4,005,593 A | 2/1977 | Goldberg |
| 3,863,933 A | 2/1975 | Tredway | 4,006,735 A | 2/1977 | Hittman et al. |
| 3,867,950 A | 2/1975 | Fischell | 4,009,375 A | 2/1977 | White et al. |
| 3,868,008 A | 2/1975 | Brumbaugh | 4,009,591 A | 3/1977 | Hester |
| 3,868,679 A | 2/1975 | Arneson | 4,010,449 A | 3/1977 | Faggin et al. |
| 3,871,599 A | 3/1975 | Takada et al. | 4,014,319 A | 3/1977 | Favre et al. |
| 3,872,285 A | 3/1975 | Shum et al. | 4,014,321 A | 3/1977 | March |
| 3,874,388 A | 4/1975 | King et al. | 4,016,764 A | 4/1977 | Rice |
| 3,876,980 A | 4/1975 | Haemmig et al. | 4,017,329 A | 4/1977 | Larson |
| 3,878,908 A | 4/1975 | Andersson et al. | 4,018,134 A | 4/1977 | Linsinger et al. |
| 3,881,528 A | 5/1975 | Mackenzie | 4,022,190 A | 5/1977 | Meyer |
| 3,893,111 A | 7/1975 | Cotter | 4,024,864 A | 5/1977 | Davies et al. |
| 3,893,451 A | 7/1975 | Durand et al. | 4,025,912 A | 5/1977 | Rice |
| 3,895,681 A | 7/1975 | Griffin et al. | 4,026,276 A | 5/1977 | Chubbuck |
| 3,899,862 A | 8/1975 | Muys et al. | 4,027,661 A | 6/1977 | Lyon et al. |
| 3,904,234 A | 9/1975 | Hill et al. | 4,031,899 A | 6/1977 | Renirie et al. |
| 3,908,334 A | 9/1975 | Rychiger | 4,036,775 A | 7/1977 | Trautvetter et al. |
| 3,908,461 A | 9/1975 | Turpen | 4,039,069 A | 8/1977 | Kwan et al. |
| 3,908,721 A | 9/1975 | McGahey et al. | 4,041,954 A | 8/1977 | Ohara et al. |
| 3,910,087 A | 10/1975 | Jones | 4,042,504 A | 8/1977 | Drori et al. |
| 3,912,168 A | 10/1975 | Mullins et al. | 4,045,345 A | 8/1977 | Drori et al. |
| 3,912,304 A | 10/1975 | Abildgaard et al. | 4,047,851 A | 9/1977 | Bender |
| 3,918,286 A | 11/1975 | Whitehead | 4,048,494 A | 9/1977 | Liesting et al. |
| 3,918,291 A | 11/1975 | Pauly et al. | 4,048,879 A | 9/1977 | Cox |
| 3,920,965 A | 11/1975 | Sohrwardy et al. | 4,049,004 A | 9/1977 | Walters |

| | | |
|---|---|---|
| 4,051,338 A | 9/1977 | Harris, III |
| 4,052,991 A | 10/1977 | Zacouto et al. |
| 4,055,074 A | 10/1977 | Thimons et al. |
| 4,055,175 A | 10/1977 | Clemens et al. |
| 4,056,854 A | 11/1977 | Boretos et al. |
| 4,058,007 A | 11/1977 | Exner et al. |
| 4,062,351 A | 12/1977 | Hastwell et al. |
| 4,062,354 A | 12/1977 | Taylor et al. |
| 4,062,360 A | 12/1977 | Bentley |
| 4,063,439 A | 12/1977 | Besson et al. |
| 4,064,882 A | 12/1977 | Johnson et al. |
| 4,070,239 A | 1/1978 | Bevilacqua |
| 4,072,047 A | 2/1978 | Reismuller et al. |
| 4,073,292 A | 2/1978 | Edelman |
| 4,075,099 A | 2/1978 | Pelton et al. |
| 4,075,602 A | 2/1978 | Clothier |
| 4,077,072 A | 3/1978 | Dezura et al. |
| 4,077,394 A | 3/1978 | McCurdy |
| 4,077,405 A | 3/1978 | Haerten et al. |
| 4,077,882 A | 3/1978 | Gangemi |
| 4,078,620 A | 3/1978 | Westlake et al. |
| 4,080,653 A | 3/1978 | Barnes, Jr. et al. |
| 4,084,752 A | 4/1978 | Hagiwara et al. |
| 4,086,488 A | 4/1978 | Hill |
| 4,087,568 A | 5/1978 | Fay et al. |
| 4,088,417 A | 5/1978 | Kosmowski |
| 4,089,329 A | 5/1978 | Couvillon, Jr. et al. |
| 4,090,802 A | 5/1978 | Bilz et al. |
| 4,092,719 A | 5/1978 | Salmon et al. |
| 4,092,925 A | 6/1978 | Fromson |
| 4,096,866 A | 6/1978 | Fischell |
| 4,098,293 A | 7/1978 | Kramer et al. |
| 4,103,496 A | 8/1978 | Colamussi et al. |
| 4,106,370 A | 8/1978 | Kraus et al. |
| 4,107,689 A | 8/1978 | Jellinek |
| 4,107,995 A | 8/1978 | Ligman et al. |
| 4,108,148 A | 8/1978 | Cannon, III |
| 4,108,575 A | 8/1978 | Schal et al. |
| 4,109,148 A | 8/1978 | Jaulmes et al. |
| 4,109,518 A | 8/1978 | Dooley et al. |
| 4,109,644 A | 8/1978 | Kojima |
| 4,111,056 A | 9/1978 | Mastromatteo |
| 4,111,629 A | 9/1978 | Nussbaumer et al. |
| 4,114,424 A | 9/1978 | Johnson |
| 4,114,606 A | 9/1978 | Seylar |
| 4,120,097 A | 10/1978 | Jeter |
| 4,120,134 A | 10/1978 | Scholle |
| 4,121,635 A | 10/1978 | Hansel |
| 4,123,310 A | 10/1978 | Varon et al. |
| 4,124,023 A | 11/1978 | Fleischmann et al. |
| 4,127,110 A | 11/1978 | Bullara |
| 4,130,169 A | 12/1978 | Denison |
| 4,131,596 A | 12/1978 | Allen |
| 4,133,355 A | 1/1979 | Mayer |
| 4,133,367 A | 1/1979 | Abell |
| 4,140,131 A | 2/1979 | Dutcher et al. |
| 4,141,348 A | 2/1979 | Hittman |
| 4,141,349 A | 2/1979 | Ory et al. |
| 4,143,661 A | 3/1979 | LaForge et al. |
| 4,146,029 A | 3/1979 | Ellinwood, Jr. |
| 4,147,161 A | 4/1979 | Ikebe et al. |
| 4,148,096 A | 4/1979 | Haas et al. |
| 4,149,423 A | 4/1979 | Frosch et al. |
| 4,151,823 A | 5/1979 | Grosse et al. |
| 4,153,085 A | 5/1979 | Adams |
| 4,156,422 A | 5/1979 | Hildebrandt et al. |
| 4,160,448 A | 7/1979 | Jackson |
| 4,160,971 A | 7/1979 | Jones et al. |
| 4,166,469 A | 9/1979 | Littleford |
| 4,167,304 A | 9/1979 | Gelbke |
| 4,167,952 A | 9/1979 | Reinicke |
| 4,168,567 A | 9/1979 | Leguy et al. |
| 4,170,280 A | 10/1979 | Schwarz |
| 4,171,218 A | 10/1979 | Hoshino et al. |
| 4,183,124 A | 1/1980 | Hoffman |
| 4,183,247 A | 1/1980 | Allen et al. |
| 4,185,641 A | 1/1980 | Minior et al. |
| 4,186,287 A | 1/1980 | Scott |
| 4,186,749 A | 2/1980 | Fryer |
| 4,186,751 A | 2/1980 | Fleischmann |
| 4,190,057 A | 2/1980 | Hill et al. |
| 4,191,004 A | 3/1980 | Gmuer et al. |
| 4,191,187 A | 3/1980 | Wright et al. |
| 4,192,192 A | 3/1980 | Schnell |
| 4,193,397 A | 3/1980 | Tucker et al. |
| 4,204,547 A | 5/1980 | Allocca |
| 4,206,755 A | 6/1980 | Klein et al. |
| 4,206,761 A | 6/1980 | Cosman |
| 4,206,762 A | 6/1980 | Cosman |
| 4,207,903 A | 6/1980 | O'Neill |
| 4,212,074 A | 7/1980 | Kuno et al. |
| 4,217,221 A | 8/1980 | Masso |
| 4,217,588 A | 8/1980 | Freeny, Jr. |
| 4,220,189 A | 9/1980 | Marquez |
| 4,221,219 A | 9/1980 | Tucker |
| 4,221,523 A | 9/1980 | Eberle |
| 4,223,837 A | 9/1980 | Gubbiotti et al. |
| 4,226,124 A | 10/1980 | Kersten et al. |
| 4,226,229 A | 10/1980 | Eckhart et al. |
| 4,227,533 A | 10/1980 | Godfrey |
| 4,231,376 A | 11/1980 | Lyon et al. |
| 4,232,682 A | 11/1980 | Veth |
| 4,237,900 A | 12/1980 | Schulman et al. |
| 4,241,247 A | 12/1980 | Byrne et al. |
| 4,241,870 A | 12/1980 | Marcus |
| 4,245,593 A | 1/1981 | Stein |
| 4,246,877 A | 1/1981 | Kennedy |
| 4,247,850 A | 1/1981 | Marcus |
| 4,248,238 A | 2/1981 | Joseph et al. |
| 4,248,241 A | 2/1981 | Tacchi |
| 4,256,094 A | 3/1981 | Kapp et al. |
| 4,256,118 A | 3/1981 | Nagel |
| 4,262,343 A | 4/1981 | Claycomb |
| 4,262,632 A | 4/1981 | Hanton et al. |
| 4,265,241 A | 5/1981 | Portner et al. |
| 4,265,252 A | 5/1981 | Chubbuck et al. |
| 4,271,018 A | 6/1981 | Drori et al. |
| 4,273,070 A | 6/1981 | Hoefelmayr et al. |
| 4,274,444 A | 6/1981 | Ruyak |
| 4,275,600 A | 6/1981 | Turner et al. |
| 4,275,913 A | 6/1981 | Marcus |
| 4,278,540 A | 7/1981 | Drori et al. |
| 4,280,036 A | 7/1981 | Fukatsu et al. |
| 4,280,775 A | 7/1981 | Wood |
| 4,281,666 A | 8/1981 | Cosman |
| 4,281,667 A | 8/1981 | Cosman |
| 4,284,073 A | 8/1981 | Krause et al. |
| 4,285,770 A | 8/1981 | Chi et al. |
| 4,291,699 A | 9/1981 | Geddes et al. |
| 4,295,963 A | 10/1981 | Drori et al. |
| 4,297,927 A | 11/1981 | Kuroda et al. |
| 4,303,075 A | 12/1981 | Heilman et al. |
| 4,305,402 A | 12/1981 | Katims |
| 4,312,374 A | 1/1982 | Drori et al. |
| 4,314,480 A | 2/1982 | Becker |
| 4,316,693 A | 2/1982 | Baxter et al. |
| 4,325,387 A | 4/1982 | Helfer |
| 4,327,804 A | 5/1982 | Reed |
| 4,328,654 A | 5/1982 | Van Ginkel et al. |
| 4,332,254 A | 6/1982 | Lundquist |
| 4,339,831 A | 7/1982 | Johnson |
| 4,342,218 A | 8/1982 | Fox |
| 4,342,308 A | 8/1982 | Trick |
| 4,346,604 A | 8/1982 | Snook et al. |
| 4,347,851 A | 9/1982 | Jundanian |
| 4,350,647 A | 9/1982 | de la Cruz |
| 4,350,970 A | 9/1982 | von Tomkewitsch et al. |
| 4,351,037 A | 9/1982 | Scherbatskoy |
| 4,351,116 A | 9/1982 | Scott, Jr. |
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Shimazoe et al. |
| 4,365,425 A | 12/1982 | Gotchel |
| 4,368,937 A | 1/1983 | Palombo et al. |
| 4,369,013 A | 1/1983 | Abildgaard et al. |

| | | | | | | |
|---|---|---|---|---|---|---|
| 4,373,527 A | 2/1983 | Fischell | | 4,499,691 A | 2/1985 | Karazim et al. |
| 4,376,523 A | 3/1983 | Goyen et al. | | 4,499,750 A | 2/1985 | Gerber et al. |
| 4,378,809 A | 4/1983 | Cosman | | 4,503,678 A | 3/1985 | Wimbush et al. |
| 4,380,427 A | 4/1983 | Hehl et al. | | 4,511,974 A | 4/1985 | Nakane et al. |
| 4,385,636 A | 5/1983 | Cosman | | 4,513,295 A | 4/1985 | Jones et al. |
| 4,386,422 A | 5/1983 | Mumby et al. | | 4,515,004 A | 5/1985 | Jaenson |
| 4,387,907 A | 6/1983 | Hiestand et al. | | 4,515,750 A | 5/1985 | Pardini et al. |
| 4,392,368 A | 7/1983 | Folkesson et al. | | 4,516,866 A | 5/1985 | Yamauchi et al. |
| 4,393,899 A | 7/1983 | Tsuji et al. | | 4,518,637 A | 5/1985 | Takeda et al. |
| 4,393,951 A | 7/1983 | Horst-Rudolf et al. | | 4,519,401 A | 5/1985 | Ko et al. |
| 4,395,232 A | 7/1983 | Koch | | 4,520,443 A | 5/1985 | Yuki et al. |
| 4,395,258 A | 7/1983 | Wang et al. | | 4,522,213 A | 6/1985 | Wallroth et al. |
| 4,395,916 A | 8/1983 | Martin | | 4,527,568 A | 7/1985 | Rickards et al. |
| 4,398,983 A | 8/1983 | Suzuki et al. | | 4,529,401 A | 7/1985 | Leslie et al. |
| 4,399,705 A | 8/1983 | Weiger et al. | | 4,531,526 A | 7/1985 | Genest |
| 4,399,707 A | 8/1983 | Wamstad | | 4,531,936 A | 7/1985 | Gordon |
| 4,399,809 A | 8/1983 | Baro et al. | | 4,536,000 A | 8/1985 | Rohm et al. |
| 4,399,821 A | 8/1983 | Bowers | | 4,537,005 A | 8/1985 | Hoyland et al. |
| 4,403,984 A | 9/1983 | Ash et al. | | 4,537,129 A | 8/1985 | Heinemann et al. |
| 4,404,968 A | 9/1983 | Evans, Sr. | | 4,538,616 A | 9/1985 | Rogoff |
| 4,404,974 A | 9/1983 | Titus | | 4,540,404 A | 9/1985 | Wolvek |
| 4,405,318 A | 9/1983 | Whitney et al. | | 4,542,461 A | 9/1985 | Eldridge et al. |
| 4,407,125 A | 10/1983 | Parsons et al. | | 4,544,369 A | 10/1985 | Skakoon et al. |
| 4,407,271 A | 10/1983 | Schiff | | 4,545,185 A | 10/1985 | Chikatani et al. |
| 4,407,296 A | 10/1983 | Anderson | | 4,546,524 A | 10/1985 | Kreft |
| 4,407,326 A | 10/1983 | Wilhelm | | 4,548,209 A | 10/1985 | Wielders et al. |
| 4,408,597 A | 10/1983 | Tenney, Jr. | | 4,552,150 A | 11/1985 | Zacouto et al. |
| 4,408,615 A | 10/1983 | Grossman | | 4,553,226 A | 11/1985 | Scherbatskoy |
| 4,415,071 A | 11/1983 | Butler et al. | | 4,556,063 A | 12/1985 | Thompson et al. |
| 4,416,282 A | 11/1983 | Saulson et al. | | 4,557,269 A | 12/1985 | Reynolds et al. |
| 4,418,899 A | 12/1983 | Zimmermann et al. | | 4,557,332 A | 12/1985 | Denison et al. |
| 4,419,393 A | 12/1983 | Hanson et al. | | 4,559,815 A | 12/1985 | Needham et al. |
| 4,421,505 A | 12/1983 | Schwartz | | 4,560,979 A | 12/1985 | Rosskopf et al. |
| 4,424,720 A | 1/1984 | Bucchianeri | | 4,561,442 A | 12/1985 | Vollmann et al. |
| 4,428,228 A | 1/1984 | Banzhaf et al. | | 4,562,751 A | 1/1986 | Nason et al. |
| 4,428,365 A | 1/1984 | Hakky et al. | | 4,563,175 A | 1/1986 | LaFond |
| 4,430,899 A | 2/1984 | Wessel et al. | | 4,565,116 A | 1/1986 | Hehl et al. |
| 4,431,009 A | 2/1984 | Marino, Jr. et al. | | 4,566,456 A | 1/1986 | Koning et al. |
| 4,431,365 A | 2/1984 | Sturtz, Jr. | | 4,569,623 A | 2/1986 | Goldmann |
| 4,432,363 A | 2/1984 | Kakegawa et al. | | 4,570,351 A | 2/1986 | Szanto et al. |
| 4,435,173 A | 3/1984 | Siposs et al. | | 4,571,161 A | 2/1986 | Leblanc et al. |
| 4,439,186 A | 3/1984 | Kuhl et al. | | 4,571,995 A | 2/1986 | Timme |
| 4,441,491 A | 4/1984 | Evans, Sr. | | 4,573,835 A | 3/1986 | Eckardt et al. |
| 4,441,501 A | 4/1984 | Parent | | 4,574,792 A | 3/1986 | Trick |
| 4,444,194 A | 4/1984 | Burcham | | 4,576,181 A | 3/1986 | Wallace et al. |
| 4,444,498 A | 4/1984 | Heinemann | | 4,576,183 A | 3/1986 | Plicchi et al. |
| 4,445,385 A | 5/1984 | Endo | | 4,577,512 A | 3/1986 | Lowenheck et al. |
| 4,446,711 A | 5/1984 | Valente | | 4,581,018 A | 4/1986 | Jassawalla et al. |
| 4,447,224 A | 5/1984 | DeCant, Jr. et al. | | 4,581,915 A | 4/1986 | Haulsee et al. |
| 4,449,493 A | 5/1984 | Kopec et al. | | 4,587,840 A | 5/1986 | Dobler et al. |
| 4,450,811 A | 5/1984 | Ichikawa et al. | | 4,589,805 A | 5/1986 | Duffner et al. |
| 4,451,033 A | 5/1984 | Nestegard | | 4,592,339 A | 6/1986 | Kuzmak et al. |
| 4,453,537 A | 6/1984 | Spitzer | | 4,592,340 A | 6/1986 | Boyles |
| 4,453,578 A | 6/1984 | Wilder | | 4,593,703 A | 6/1986 | Cosman |
| 4,460,835 A | 7/1984 | Masuoka | | 4,595,228 A | 6/1986 | Chu |
| 4,464,170 A | 8/1984 | Clemens et al. | | 4,596,563 A | 6/1986 | Pande |
| 4,465,015 A | 8/1984 | Osta et al. | | 4,599,943 A | 7/1986 | Kobler et al. |
| 4,465,474 A | 8/1984 | Mardorf et al. | | 4,600,855 A | 7/1986 | Strachan et al. |
| 4,466,290 A | 8/1984 | Frick | | 4,602,541 A | 7/1986 | Benzinger et al. |
| 4,468,172 A | 8/1984 | Dixon et al. | | 4,604,089 A | 8/1986 | Santangelo et al. |
| 4,468,762 A | 8/1984 | Jurgens et al. | | 4,605,354 A | 8/1986 | Daly |
| 4,469,365 A | 9/1984 | Marcus et al. | | 4,606,419 A | 8/1986 | Perini |
| 4,471,182 A | 9/1984 | Wielgos et al. | | 4,606,478 A | 8/1986 | Hack et al. |
| 4,471,786 A | 9/1984 | Inagaki et al. | | 4,610,256 A | 9/1986 | Wallace |
| 4,473,067 A | 9/1984 | Schiff | | 4,614,137 A | 9/1986 | Jones |
| 4,473,078 A | 9/1984 | Angel | | 4,617,016 A | 10/1986 | Blomberg et al. |
| 4,476,721 A | 10/1984 | Hochreuther et al. | | 4,618,861 A | 10/1986 | Gettens et al. |
| 4,478,213 A | 10/1984 | Redding | | 4,620,807 A | 11/1986 | Polit |
| 4,478,538 A | 10/1984 | Kakino et al. | | 4,621,331 A | 11/1986 | Iwata et al. |
| 4,483,196 A | 11/1984 | Kurtz et al. | | 4,622,871 A | 11/1986 | Van Sickle et al. |
| 4,484,135 A | 11/1984 | Ishihara et al. | | 4,626,462 A | 12/1986 | Kober et al. |
| 4,485,813 A | 12/1984 | Anderson et al. | | 4,633,304 A | 12/1986 | Nagasaki et al. |
| 4,489,916 A | 12/1984 | Stevens | | 4,633,878 A | 1/1987 | Bombardieri et al. |
| 4,492,632 A | 1/1985 | Mattson | | 4,635,182 A | 1/1987 | Hintz |
| 4,494,411 A | 1/1985 | Koschke et al. | | 4,637,736 A | 1/1987 | Andeen et al. |
| 4,494,950 A | 1/1985 | Fischell | | 4,638,665 A | 1/1987 | Benson et al. |
| 4,497,176 A | 2/1985 | Rubin et al. | | 4,644,246 A | 2/1987 | Knapen et al. |
| 4,497,201 A | 2/1985 | Allen et al. | | 4,646,553 A | 3/1987 | Tufte et al. |
| 4,499,394 A | 2/1985 | Koal | | 4,648,363 A | 3/1987 | Kronich |

| | | | | | | |
|---|---|---|---|---|---|---|
| 4,648,406 A | 3/1987 | Miller | | 4,803,987 A | 2/1989 | Calfee et al. |
| 4,658,358 A | 4/1987 | Leach et al. | | 4,804,368 A | 2/1989 | Skakoon et al. |
| 4,658,760 A | 4/1987 | Zebuhr | | 4,807,321 A | 2/1989 | Grasselli et al. |
| 4,660,568 A | 4/1987 | Cosman | | 4,808,167 A | 2/1989 | Mann et al. |
| 4,665,511 A | 5/1987 | Rodney et al. | | 4,812,823 A | 3/1989 | Dickerson |
| 4,665,896 A | 5/1987 | LaForge et al. | | 4,819,656 A | 4/1989 | Spector |
| 4,669,484 A | 6/1987 | Masters | | 4,820,265 A | 4/1989 | DeSatnick et al. |
| 4,672,974 A | 6/1987 | Lee | | 4,820,953 A | 4/1989 | Saubolle et al. |
| 4,674,457 A | 6/1987 | Berger et al. | | 4,821,167 A | 4/1989 | Wiebe |
| 4,674,546 A | 6/1987 | Fournier et al. | | 4,821,723 A | 4/1989 | Baker, Jr. et al. |
| 4,678,408 A | 7/1987 | Nason et al. | | 4,823,779 A | 4/1989 | Daly et al. |
| 4,681,559 A | 7/1987 | Hooven | | 4,830,006 A | 5/1989 | Haluska et al. |
| 4,683,850 A | 8/1987 | Bauder et al. | | 4,832,034 A | 5/1989 | Pizziconi et al. |
| 4,685,463 A | 8/1987 | Williams | | 4,833,384 A | 5/1989 | Munro et al. |
| 4,685,469 A | 8/1987 | Keller et al. | | 4,834,731 A | 5/1989 | Nowak et al. |
| 4,685,903 A | 8/1987 | Cable et al. | | 4,838,857 A | 6/1989 | Strowe et al. |
| 4,686,987 A | 8/1987 | Salo et al. | | 4,840,068 A | 6/1989 | Mayhew, Jr. |
| 4,687,530 A | 8/1987 | Berscheid et al. | | 4,840,350 A | 6/1989 | Cook et al. |
| 4,689,979 A | 9/1987 | Otsuka et al. | | 4,844,002 A | 7/1989 | Yasui et al. |
| 4,691,694 A | 9/1987 | Boyd et al. | | 4,846,153 A | 7/1989 | Berci |
| 4,691,710 A | 9/1987 | Dickens et al. | | 4,846,191 A | 7/1989 | Brockway et al. |
| 4,693,253 A | 9/1987 | Adams | | 4,846,664 A | 7/1989 | Hehl et al. |
| 4,695,237 A | 9/1987 | Inaba et al. | | 4,854,328 A | 8/1989 | Pollack |
| 4,696,189 A | 9/1987 | Hochreuther et al. | | 4,863,470 A | 9/1989 | Carter |
| 4,697,574 A | 10/1987 | Karcher et al. | | 4,865,587 A | 9/1989 | Walling |
| 4,698,038 A | 10/1987 | Key et al. | | 4,867,160 A | 9/1989 | Schaldach et al. |
| 4,700,497 A | 10/1987 | Sato et al. | | 4,867,498 A | 9/1989 | Delphia et al. |
| 4,700,610 A | 10/1987 | Bauer et al. | | 4,867,618 A | 9/1989 | Brohammer |
| 4,701,143 A | 10/1987 | Key et al. | | 4,869,252 A | 9/1989 | Gilli |
| 4,703,756 A | 11/1987 | Gough et al. | | 4,870,258 A | 9/1989 | Mochizuki et al. |
| 4,705,507 A | 11/1987 | Boyles | | 4,871,351 A | 10/1989 | Feingold et al. |
| 4,706,948 A | 11/1987 | Kroecher et al. | | 4,872,483 A | 10/1989 | Shah |
| 4,712,562 A | 12/1987 | Ohayon et al. | | 4,872,869 A | 10/1989 | Johns |
| 4,718,425 A | 1/1988 | Tanaka et al. | | 4,873,677 A | 10/1989 | Sakamoto et al. |
| 4,722,348 A | 2/1988 | Ligtenberg et al. | | 4,875,483 A | 10/1989 | Vollmann et al. |
| 4,724,806 A | 2/1988 | Hartwig et al. | | 4,880,004 A | 11/1989 | Baker, Jr. et al. |
| 4,724,830 A | 2/1988 | Fischell | | 4,882,678 A | 11/1989 | Hollis et al. |
| 4,725,826 A | 2/1988 | Hunter | | 4,886,392 A | 12/1989 | Iio et al. |
| 4,728,479 A | 3/1988 | Merkovsky | | 4,895,151 A | 1/1990 | Grevis et al. |
| 4,729,517 A | 3/1988 | Krokor et al. | | 4,896,594 A | 1/1990 | Baur et al. |
| 4,730,188 A | 3/1988 | Milheiser | | 4,898,158 A | 2/1990 | Daly et al. |
| 4,730,420 A | 3/1988 | Stratmann et al. | | 4,898,578 A | 2/1990 | Rubalcaba, Jr. |
| 4,730,619 A | 3/1988 | Koning et al. | | 4,899,751 A | 2/1990 | Cohen |
| 4,731,058 A | 3/1988 | Doan | | 4,899,752 A | 2/1990 | Cohen |
| 4,735,205 A | 4/1988 | Chachques et al. | | 4,902,277 A | 2/1990 | Mathies et al. |
| 4,738,267 A | 4/1988 | Lazorthes et al. | | 4,903,701 A | 2/1990 | Moore et al. |
| 4,738,268 A | 4/1988 | Kipnis | | 4,909,678 A | 3/1990 | Kakimoto et al. |
| 4,741,345 A | 5/1988 | Matthews et al. | | 4,913,147 A | 4/1990 | Fahlstrom et al. |
| 4,741,732 A | 5/1988 | Crankshaw et al. | | 4,919,143 A | 4/1990 | Ayers |
| 4,743,129 A | 5/1988 | Keryhuel et al. | | 4,924,872 A | 5/1990 | Frank |
| 4,745,541 A | 5/1988 | Vaniglia et al. | | 4,926,903 A | 5/1990 | Kawai et al. |
| 4,746,830 A | 5/1988 | Holland | | 4,932,406 A | 6/1990 | Berkovits |
| 4,750,495 A | 6/1988 | Moore et al. | | 4,934,369 A | 6/1990 | Maxwell |
| 4,752,115 A | 6/1988 | Murray, Jr. et al. | | 4,936,304 A | 6/1990 | Kresh et al. |
| 4,752,658 A | 6/1988 | Mack | | 4,940,037 A | 7/1990 | Eckert et al. |
| 4,757,463 A | 7/1988 | Ballou et al. | | 4,941,718 A | 7/1990 | Alexander, III et al. |
| 4,759,386 A | 7/1988 | Grouw, III | | 4,942,004 A | 7/1990 | Catanzaro |
| 4,763,649 A | 8/1988 | Merrick | | 4,944,050 A | 7/1990 | Shames et al. |
| 4,765,001 A | 8/1988 | Smith | | 4,944,298 A | 7/1990 | Sholder |
| 4,767,406 A | 8/1988 | Wadham et al. | | 4,944,307 A | 7/1990 | Hon et al. |
| 4,769,001 A | 9/1988 | Prince | | 4,945,761 A | 8/1990 | Lessi et al. |
| 4,772,896 A | 9/1988 | Nakatsu et al. | | 4,949,724 A | 8/1990 | Mahutte et al. |
| 4,773,401 A | 9/1988 | Citak et al. | | 4,952,205 A | 8/1990 | Mauerer et al. |
| 4,774,950 A | 10/1988 | Cohen | | 4,952,928 A | 8/1990 | Carroll et al. |
| 4,774,955 A | 10/1988 | Jones | | 4,953,563 A | 9/1990 | Kaiser et al. |
| 4,777,953 A | 10/1988 | Ash et al. | | 4,954,677 A | 9/1990 | Alberter et al. |
| 4,779,626 A | 10/1988 | Peel et al. | | 4,958,630 A | 9/1990 | Rosenbluth et al. |
| 4,781,192 A | 11/1988 | Demer | | 4,958,645 A | 9/1990 | Cadell et al. |
| 4,782,826 A | 11/1988 | Fogarty | | 4,960,424 A | 10/1990 | Grooters |
| 4,783,106 A | 11/1988 | Nutter | | 4,960,966 A | 10/1990 | Evans et al. |
| 4,788,847 A | 12/1988 | Sterghos | | 4,967,585 A | 11/1990 | Grimaldo |
| 4,791,318 A | 12/1988 | Lewis et al. | | 4,967,761 A | 11/1990 | Nathanielsz |
| 4,794,803 A | 1/1989 | Osterhout et al. | | 4,970,823 A | 11/1990 | Chen et al. |
| 4,796,641 A | 1/1989 | Mills et al. | | 4,971,251 A | 11/1990 | Dobrick et al. |
| 4,798,211 A | 1/1989 | Goor et al. | | 4,977,896 A | 12/1990 | Robinson et al. |
| 4,798,227 A | 1/1989 | Goodwin | | 4,978,335 A | 12/1990 | Arthur, III |
| 4,799,491 A | 1/1989 | Eckerle | | 4,978,338 A | 12/1990 | Melsky et al. |
| 4,799,625 A | 1/1989 | Weaver, Jr. et al. | | 4,979,730 A | 12/1990 | Holbrook et al. |
| 4,802,488 A | 2/1989 | Eckerle | | 4,980,671 A | 12/1990 | McCurdy |

| Patent No. | Date | Inventor(s) |
|---|---|---|
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |

| | | | | | | |
|---|---|---|---|---|---|---|
| 5,298,022 A | 3/1994 | Bernardi et al. | | 5,507,412 A | 4/1996 | Ebert et al. |
| 5,298,884 A | 3/1994 | Gilmore et al. | | 5,507,737 A | 4/1996 | Palmskog et al. |
| 5,300,093 A | 4/1994 | Koestner et al. | | 5,507,785 A | 4/1996 | Deno |
| 5,300,120 A | 4/1994 | Knapp et al. | | 5,509,888 A | 4/1996 | Miller |
| 5,304,112 A | 4/1994 | Mrklas et al. | | 5,509,891 A | 4/1996 | DeRidder |
| 5,305,923 A | 4/1994 | Kirschner et al. | | 5,513,945 A | 5/1996 | Hartmann et al. |
| 5,312,443 A | 5/1994 | Adams et al. | | 5,514,103 A | 5/1996 | Srisathapat et al. |
| 5,312,452 A | 5/1994 | Salo | | 5,518,504 A | 5/1996 | Polyak |
| 5,312,453 A | 5/1994 | Shelton et al. | | 5,520,606 A | 5/1996 | Schoolman et al. |
| 5,313,953 A | 5/1994 | Yomtov et al. | | 5,523,740 A | 6/1996 | Burgmann |
| 5,314,451 A | 5/1994 | Mulier | | 5,534,018 A | 7/1996 | Wahlstrand et al. |
| 5,314,457 A | 5/1994 | Jeutter et al. | | 5,535,752 A | 7/1996 | Halperin et al. |
| 5,318,545 A * | 6/1994 | Tucker .......................... 604/244 | | 5,538,005 A | 7/1996 | Harrison et al. |
| 5,324,315 A | 6/1994 | Grevious | | 5,541,857 A | 7/1996 | Walter et al. |
| 5,325,834 A | 7/1994 | Ballheimer et al. | | 5,545,140 A | 8/1996 | Conero et al. |
| 5,326,249 A | 7/1994 | Weissfloch | | 5,545,151 A | 8/1996 | O'Connor et al. |
| 5,328,460 A | 7/1994 | Lord et al. | | 5,545,186 A | 8/1996 | Olson et al. |
| 5,330,511 A | 7/1994 | Boute | | 5,545,214 A | 8/1996 | Stevens |
| 5,337,750 A | 8/1994 | Walloch | | 5,547,470 A | 8/1996 | Johnson et al. |
| 5,341,430 A | 8/1994 | Aulia et al. | | 5,551,427 A | 9/1996 | Altman |
| 5,342,401 A | 8/1994 | Spano et al. | | 5,551,439 A | 9/1996 | Hickey |
| 5,342,406 A | 8/1994 | Thompson | | 5,554,185 A | 9/1996 | Block et al. |
| 5,344,388 A | 9/1994 | Maxwell et al. | | 5,558,644 A | 9/1996 | Boyd et al. |
| 5,347,476 A | 9/1994 | McBean, Sr. | | 5,564,434 A | 10/1996 | Halperin et al. |
| 5,348,210 A | 9/1994 | Linzell et al. | | 5,575,770 A | 11/1996 | Melsky et al. |
| 5,348,536 A | 9/1994 | Young et al. | | 5,584,803 A | 12/1996 | Stevens et al. |
| 5,350,413 A | 9/1994 | Miller et al. | | 5,586,629 A | 12/1996 | Shoberg et al. |
| 5,352,180 A | 10/1994 | Candelon et al. | | 5,593,430 A | 1/1997 | Renger |
| 5,353,622 A | 10/1994 | Theener | | 5,594,665 A | 1/1997 | Walter et al. |
| 5,353,800 A | 10/1994 | Pohndorf et al. | | 5,596,986 A | 1/1997 | Goldfarb |
| 5,354,200 A | 10/1994 | Klein et al. | | 5,597,284 A | 1/1997 | Weltlich et al. |
| 5,354,316 A | 10/1994 | Keimel | | 5,610,083 A | 3/1997 | Chan et al. |
| 5,354,319 A | 10/1994 | Wyborny et al. | | 5,611,768 A | 3/1997 | Tutrone, Jr. |
| 5,360,407 A | 11/1994 | Leonard et al. | | 5,612,497 A | 3/1997 | Walter et al. |
| 5,365,462 A | 11/1994 | McBean, Sr. | | 5,615,671 A | 4/1997 | Schoonen et al. |
| 5,365,619 A | 11/1994 | Solomon | | 5,619,991 A | 4/1997 | Sloane |
| 5,365,985 A | 11/1994 | Todd et al. | | 5,625,946 A | 5/1997 | Wildeson et al. |
| 5,368,040 A | 11/1994 | Carney | | 5,626,623 A | 5/1997 | Kieval et al. |
| 5,370,665 A | 12/1994 | Hudrlik | | 5,626,630 A | 5/1997 | Markowitz et al. |
| 5,373,852 A | 12/1994 | Harrison et al. | | 5,630,836 A | 5/1997 | Prem et al. |
| 5,375,073 A | 12/1994 | McBean | | 5,634,255 A | 6/1997 | Bishop et al. |
| 5,377,128 A | 12/1994 | McBean | | 5,637,083 A | 6/1997 | Bertrand et al. |
| 5,378,231 A | 1/1995 | Johnson et al. | | 5,643,207 A | 7/1997 | Rise |
| 5,382,232 A | 1/1995 | Hague et al. | | 5,645,116 A | 7/1997 | McDonald |
| 5,383,915 A | 1/1995 | Adams | | 5,650,766 A | 7/1997 | Burgmann et al. |
| 5,388,578 A | 2/1995 | Yomtov et al. | | 5,673,585 A | 10/1997 | Bishop et al. |
| 5,388,586 A | 2/1995 | Lee et al. | | 5,676,690 A | 10/1997 | Noren et al. |
| 5,388,831 A | 2/1995 | Quadri et al. | | 5,681,285 A | 10/1997 | Ford et al. |
| 5,394,909 A | 3/1995 | Mitchell et al. | | 5,686,831 A | 11/1997 | Vandervalk et al. |
| 5,402,944 A | 4/1995 | Pape et al. | | 5,687,734 A | 11/1997 | Dempsey et al. |
| 5,406,957 A | 4/1995 | Tansey | | 5,693,076 A | 12/1997 | Kaemmerer |
| 5,409,009 A | 4/1995 | Olson | | 5,702,368 A | 12/1997 | Stevens et al. |
| 5,411,031 A | 5/1995 | Yomtov | | 5,702,427 A | 12/1997 | Ecker et al. |
| 5,411,551 A | 5/1995 | Winston et al. | | 5,702,431 A | 12/1997 | Wang et al. |
| 5,411,552 A | 5/1995 | Andersen et al. | | 5,704,352 A | 1/1998 | Tremblay et al. |
| 5,416,372 A | 5/1995 | Ljungstroem et al. | | 5,715,786 A | 2/1998 | Seiberth et al. |
| 5,417,226 A | 5/1995 | Juma | | 5,715,837 A | 2/1998 | Chen |
| 5,417,717 A | 5/1995 | Salo et al. | | 5,720,436 A | 2/1998 | Buschor et al. |
| 5,425,362 A | 6/1995 | Siker et al. | | 5,730,101 A | 3/1998 | Aupperle et al. |
| 5,431,171 A | 7/1995 | Harrison et al. | | 5,732,710 A | 3/1998 | Rabinovich et al. |
| 5,431,694 A | 7/1995 | Snaper et al. | | 5,733,313 A | 3/1998 | Barreras, Sr. et al. |
| 5,433,694 A | 7/1995 | Lim et al. | | 5,738,652 A | 4/1998 | Boyd et al. |
| 5,437,605 A | 8/1995 | Helmy et al. | | 5,742,233 A | 4/1998 | Hoffman et al. |
| 5,443,215 A | 8/1995 | Fackler | | 5,743,267 A | 4/1998 | Nikolic et al. |
| 5,447,519 A | 9/1995 | Peterson | | 5,749,369 A | 5/1998 | Rabinovich et al. |
| 5,449,368 A | 9/1995 | Kuzmak | | 5,749,909 A | 5/1998 | Schroeppel et al. |
| 5,456,690 A | 10/1995 | Duong-Van | | 5,755,687 A | 5/1998 | Donlon |
| 5,461,390 A | 10/1995 | Hoshen | | 5,755,748 A | 5/1998 | Borza et al. |
| 5,464,435 A | 11/1995 | Neumann | | 5,758,667 A * | 6/1998 | Slettenmark .................. 128/899 |
| 5,467,627 A | 11/1995 | Smith et al. | | 5,765,568 A | 6/1998 | Sweezer, Jr. et al. |
| 5,474,226 A | 12/1995 | Joseph | | 5,769,812 A | 6/1998 | Stevens et al. |
| 5,479,818 A | 1/1996 | Walter et al. | | 5,771,903 A | 6/1998 | Jakobsson |
| 5,482,049 A | 1/1996 | Addiss et al. | | 5,782,774 A | 7/1998 | Shmulewitz |
| 5,487,760 A | 1/1996 | Villafana | | 5,787,520 A | 8/1998 | Dunbar |
| 5,493,738 A | 2/1996 | Sanderson et al. | | 5,791,344 A | 8/1998 | Schulman et al. |
| 5,494,036 A | 2/1996 | Uber, III et al. | | 5,792,094 A | 8/1998 | Stevens et al. |
| 5,494,193 A | 2/1996 | Kirschner et al. | | 5,792,179 A | 8/1998 | Sideris |
| 5,504,474 A | 4/1996 | Libman et al. | | 5,795,325 A | 8/1998 | Valley et al. |
| 5,505,916 A | 4/1996 | Berry, Jr. | | 5,796,827 A | 8/1998 | Coppersmith et al. |

| Patent | Type | Date | Inventor |
|---|---|---|---|
| 5,800,375 | A | 9/1998 | Sweezer et al. |
| 5,807,265 | A | 9/1998 | Itoigawa et al. |
| 5,807,336 | A | 9/1998 | Russo et al. |
| 5,810,015 | A | 9/1998 | Flaherty |
| 5,810,757 | A | 9/1998 | Sweezer, Jr. et al. |
| 5,814,016 | A | 9/1998 | Valley et al. |
| 5,817,093 | A | 10/1998 | Williamson, IV et al. |
| 5,833,603 | A | 11/1998 | Kovacs et al. |
| 5,836,300 | A | 11/1998 | Mault |
| 5,836,886 | A | 11/1998 | Itoigawa et al. |
| 5,840,081 | A | 11/1998 | Andersen et al. |
| 5,849,225 | A | 12/1998 | Ebina et al. |
| 5,855,597 | A | 1/1999 | Jayaraman et al. |
| 5,855,601 | A | 1/1999 | Bessler et al. |
| 5,860,938 | A | 1/1999 | Lafontaine et al. |
| 5,861,018 | A | 1/1999 | Feierbach |
| 5,863,366 | A | 1/1999 | Snow |
| 5,868,702 | A | 2/1999 | Stevens et al. |
| 5,873,837 | A | 2/1999 | Lieber et al. |
| 5,875,953 | A | 3/1999 | Shioya et al. |
| 5,879,499 | A | 3/1999 | Corvi |
| 5,881,919 | A | 3/1999 | Womac et al. |
| 5,885,238 | A | 3/1999 | Stevens et al. |
| 5,887,475 | A | 3/1999 | Muldner |
| 5,899,927 | A | 5/1999 | Ecker et al. |
| 5,916,179 | A | 6/1999 | Sharrock |
| 5,916,237 | A | 6/1999 | Schu |
| 5,935,078 | A | 8/1999 | Feierbach |
| 5,938,669 | A | 8/1999 | Klaiber et al. |
| 5,951,487 | A | 9/1999 | Brehmeier-Flick et al. |
| 5,957,861 | A | 9/1999 | Combs et al. |
| 5,967,986 | A | 10/1999 | Cimochowski et al. |
| 5,971,934 | A | 10/1999 | Scherer et al. |
| 5,974,873 | A | 11/1999 | Nelson et al. |
| 5,978,985 | A | 11/1999 | Thurman |
| 5,995,874 | A | 11/1999 | Borza et al. |
| 6,015,386 | A | 1/2000 | Kensey et al. |
| 6,015,387 | A | 1/2000 | Schwartz et al. |
| 6,019,729 | A | 2/2000 | Itoigawa et al. |
| 6,024,704 | A | 2/2000 | Meador et al. |
| 6,030,413 | A | 2/2000 | Lazarus |
| 6,035,461 | A | 3/2000 | Nguyen |
| 6,053,873 | A | 4/2000 | Govari et al. |
| 6,056,723 | A | 5/2000 | Donlon |
| 6,058,330 | A | 5/2000 | Borza et al. |
| 6,059,757 | A | 5/2000 | Macoviak et al. |
| 6,067,474 | A | 5/2000 | Schulman et al. |
| 6,067,991 | A * | 5/2000 | Forsell .................... 128/899 |
| 6,076,016 | A | 6/2000 | Feierbach |
| 6,083,174 | A | 7/2000 | Brehmeier-Flick et al. |
| 6,090,096 | A | 7/2000 | St. Goar et al. |
| 6,102,678 | A | 8/2000 | Peclat et al. |
| 6,102,856 | A | 8/2000 | Groff et al. |
| 6,102,922 | A | 8/2000 | Jakobsson et al. |
| 6,106,477 | A | 8/2000 | Miesel et al. |
| 6,106,551 | A | 8/2000 | Crossett et al. |
| 6,110,145 | A | 8/2000 | Macoviak |
| 6,113,553 | A | 9/2000 | Chubbuck |
| 6,131,664 | A | 10/2000 | Sonnier |
| 6,135,945 | A | 10/2000 | Sultan |
| 6,159,156 | A | 12/2000 | Van Bockel et al. |
| 6,162,180 | A | 12/2000 | Miesel et al. |
| 6,162,245 | A | 12/2000 | Jayaraman et al. |
| 6,168,614 | B1 | 1/2001 | Andersen et al. |
| 6,234,745 | B1 | 5/2001 | Pugh et al. |
| 6,240,316 | B1 | 5/2001 | Richmond et al. |
| 6,240,318 | B1 | 5/2001 | Phillips |
| 6,245,102 | B1 | 6/2001 | Jayaraman |
| 6,248,080 | B1 | 6/2001 | Miesel et al. |
| 6,251,093 | B1 | 6/2001 | Valley et al. |
| 6,269,819 | B1 | 8/2001 | Oz et al. |
| 6,277,078 | B1 | 8/2001 | Porat et al. |
| 6,292,697 | B1 | 9/2001 | Roberts |
| 6,309,350 | B1 | 10/2001 | VanTassel et al. |
| 6,315,769 | B1 | 11/2001 | Peer et al. |
| 6,319,208 | B1 | 11/2001 | Abita et al. |
| 6,328,699 | B1 | 12/2001 | Eigler et al. |
| 6,338,735 | B1 | 1/2002 | Stevens |
| 6,357,438 | B1 | 3/2002 | Hansen |
| 6,360,122 | B1 | 3/2002 | Fischell et al. |
| 6,360,822 | B1 | 3/2002 | Robertson et al. |
| 6,366,817 | B1 | 4/2002 | Kung |
| 6,379,308 | B1 | 4/2002 | Brockway et al. |
| 6,379,380 | B1 | 4/2002 | Satz |
| 6,398,752 | B1 | 6/2002 | Sweezer, Jr. et al. |
| 6,409,674 | B1 | 6/2002 | Brockway et al. |
| 6,423,031 | B1 | 7/2002 | Donlon |
| 6,430,444 | B1 | 8/2002 | Borza et al. |
| 6,431,175 | B1 | 8/2002 | Penner et al. |
| 6,432,040 | B1 | 8/2002 | Meah |
| 6,443,887 | B1 | 9/2002 | Derus et al. |
| 6,443,893 | B1 | 9/2002 | Schnakenberg et al. |
| 6,450,173 | B1 | 9/2002 | Forsell et al. |
| 6,450,946 | B1 | 9/2002 | Forsell et al. |
| 6,453,907 | B1 | 9/2002 | Forsell et al. |
| 6,454,698 | B1 | 9/2002 | Forsell et al. |
| 6,454,699 | B1 | 9/2002 | Forsell et al. |
| 6,454,700 | B1 | 9/2002 | Forsell et al. |
| 6,454,701 | B1 | 9/2002 | Forsell et al. |
| 6,461,292 | B1 | 10/2002 | Forsell et al. |
| 6,461,293 | B1 | 10/2002 | Forsell et al. |
| 6,463,329 | B1 | 10/2002 | Goedeke |
| 6,463,935 | B1 | 10/2002 | Forsell et al. |
| 6,464,628 | B1 | 10/2002 | Forsell et al. |
| 6,470,212 | B1 | 10/2002 | Weijand et al. |
| 6,470,892 | B1 | 10/2002 | Forsell et al. |
| 6,471,635 | B1 | 10/2002 | Forsell et al. |
| 6,475,136 | B1 | 11/2002 | Forsell et al. |
| 6,475,170 | B1 | 11/2002 | Doron et al. |
| 6,482,145 | B1 | 11/2002 | Forsell et al. |
| 6,482,171 | B1 | 11/2002 | Corvi et al. |
| 6,482,177 | B1 | 11/2002 | Leinders et al. |
| 6,486,588 | B2 | 11/2002 | Doron et al. |
| 6,503,189 | B1 | 1/2003 | Forsell |
| 6,504,286 | B1 | 1/2003 | Porat et al. |
| 6,531,739 | B2 | 3/2003 | Cable et al. |
| 6,533,719 | B2 | 3/2003 | Kuyava et al. |
| 6,533,733 | B1 | 3/2003 | Ericson et al. |
| 6,542,350 | B1 | 4/2003 | Rogers |
| 6,558,321 | B1 | 5/2003 | Burd et al. |
| 6,558,994 | B2 | 5/2003 | Cha et al. |
| 6,573,563 | B2 | 6/2003 | Lee et al. |
| 6,582,462 | B1 | 6/2003 | Andersen et al. |
| 6,599,250 | B2 | 7/2003 | Webb et al. |
| 6,605,112 | B1 | 8/2003 | Moll et al. |
| 6,629,534 | B1 | 10/2003 | St. Goar et al. |
| 6,640,137 | B2 | 10/2003 | MacDonald |
| 6,641,610 | B2 | 11/2003 | Wolf et al. |
| 6,645,143 | B2 | 11/2003 | VanTassel et al. |
| 6,673,109 | B2 | 1/2004 | Cox |
| 6,678,561 | B2 | 1/2004 | Forsell et al. |
| 6,682,480 | B1 | 1/2004 | Habib et al. |
| 6,682,503 | B1 | 1/2004 | Fariss et al. |
| 6,682,559 | B2 | 1/2004 | Myers et al. |
| 6,695,866 | B1 | 2/2004 | Kuehn et al. |
| 6,709,385 | B2 | 3/2004 | Forsell et al. |
| 6,718,200 | B2 | 4/2004 | Marmaropoulos et al. |
| 6,719,787 | B2 | 4/2004 | Cox |
| 6,719,788 | B2 | 4/2004 | Cox |
| 6,719,789 | B2 | 4/2004 | Cox |
| 6,731,976 | B2 | 5/2004 | Penn et al. |
| 6,733,525 | B2 | 5/2004 | Pease et al. |
| 6,736,846 | B2 | 5/2004 | Cox |
| 6,752,813 | B2 | 6/2004 | Goldfarb et al. |
| 6,796,942 | B1 | 9/2004 | Kreiner et al. |
| 6,822,343 | B2 | 11/2004 | Estevez |
| 6,851,628 | B1 | 2/2005 | Garrison et al. |
| 6,855,115 | B2 | 2/2005 | Fonseca et al. |
| 6,889,772 | B2 | 5/2005 | Buytaert et al. |
| 6,890,300 | B2 | 5/2005 | Lloyd et al. |
| 6,896,651 | B2 | 5/2005 | Gross et al. |
| 6,896,690 | B1 | 5/2005 | Lambrecht et al. |
| 6,913,600 | B2 | 7/2005 | Valley et al. |
| 6,915,165 | B2 | 7/2005 | Forsell et al. |
| 6,926,246 | B2 | 8/2005 | Ginggen et al. |
| 6,929,653 | B2 | 8/2005 | Strecter |
| 6,932,792 | B1 | 8/2005 | St. Goar et al. |
| 6,951,229 | B2 | 10/2005 | Garrison et al. |

| | | | |
|---|---|---|---|
| 6,951,571 B1 | 10/2005 | Srivastava | |
| 6,953,429 B2 | 10/2005 | Forsell et al. | |
| 6,961,619 B2 | 11/2005 | Casey | |
| 6,970,742 B2 | 11/2005 | Mann et al. | |
| 6,979,350 B2 | 12/2005 | Moll et al. | |
| 6,985,078 B2 | 1/2006 | Suzuki et al. | |
| 6,989,027 B2 | 1/2006 | Allen et al. | |
| 7,011,095 B2 | 3/2006 | Wolf et al. | |
| 7,011,624 B2 | 3/2006 | Forsell et al. | |
| 7,017,583 B2 | 3/2006 | Forsell et al. | |
| 7,018,406 B2 | 3/2006 | Seguin et al. | |
| 7,021,402 B2 | 4/2006 | Beato et al. | |
| 7,025,727 B2 | 4/2006 | Brockway et al. | |
| 7,044,920 B2 | 5/2006 | Letort | |
| 7,060,080 B2 | 6/2006 | Bachmann et al. | |
| 7,081,683 B2 | 7/2006 | Ariav et al. | |
| 7,109,933 B2 | 9/2006 | Ito et al. | |
| 7,131,447 B2 | 11/2006 | Sterman et al. | |
| 7,131,945 B2 | 11/2006 | Fink et al. | |
| 7,134,580 B2 | 11/2006 | Garrison et al. | |
| 7,144,400 B2 | 12/2006 | Byrum et al. | |
| 7,147,640 B2 | 12/2006 | Huebner et al. | |
| 7,153,262 B2 | 12/2006 | Stivoric et al. | |
| 7,187,978 B2 | 3/2007 | Malek et al. | |
| 7,225,032 B2 | 5/2007 | Schmeling et al. | |
| 7,257,438 B2 | 8/2007 | Kinast | |
| 7,285,090 B2 | 10/2007 | Stivoric et al. | |
| 2001/0011543 A1 | 8/2001 | Forsell | |
| 2001/0041823 A1 | 11/2001 | Snyder et al. | |
| 2002/0049394 A1 | 4/2002 | Roy et al. | |
| 2002/0120200 A1 | 8/2002 | Brockway et al. | |
| 2002/0138009 A1 | 9/2002 | Brockway et al. | |
| 2002/0177782 A1 | 11/2002 | Penner | |
| 2003/0009201 A1 | 1/2003 | Forsell | |
| 2003/0030893 A1 | 2/2003 | Cornelius et al. | |
| 2003/0032857 A1 | 2/2003 | Forsell | |
| 2003/0037591 A1 | 2/2003 | Ashton et al. | |
| 2003/0045775 A1 | 3/2003 | Forsell | |
| 2003/0066536 A1 | 4/2003 | Forsell | |
| 2003/0088148 A1 | 5/2003 | Forsell | |
| 2003/0092962 A1 | 5/2003 | Forsell | |
| 2003/0093117 A1 | 5/2003 | Saadat | |
| 2003/0100929 A1 | 5/2003 | Forsell | |
| 2003/0105385 A1 | 6/2003 | Forsell | |
| 2003/0109771 A1 | 6/2003 | Forsell | |
| 2003/0114729 A1 | 6/2003 | Forsell | |
| 2003/0125605 A1 | 7/2003 | Forsell | |
| 2003/0125768 A1 | 7/2003 | Peter | |
| 2003/0135089 A1 | 7/2003 | Forsell | |
| 2003/0135090 A1 | 7/2003 | Forsell | |
| 2003/0136417 A1 | 7/2003 | Fonseca et al. | |
| 2003/0144648 A1 | 7/2003 | Forsell | |
| 2003/0163079 A1 | 8/2003 | Burnett | |
| 2003/0216666 A1 | 11/2003 | Ericson et al. | |
| 2004/0054352 A1 | 3/2004 | Adams et al. | |
| 2004/0113790 A1 | 6/2004 | Hamel et al. | |
| 2004/0133092 A1 | 7/2004 | Kain | |
| 2004/0147969 A1 | 7/2004 | Mann et al. | |
| 2004/0172087 A1 | 9/2004 | Forsell | |
| 2004/0186396 A1 | 9/2004 | Roy et al. | |
| 2004/0254537 A1 | 12/2004 | Conlon et al. | |
| 2005/0015014 A1 | 1/2005 | Fonseca et al. | |
| 2005/0025979 A1 | 2/2005 | Sandt et al. | |
| 2005/0027175 A1 | 2/2005 | Yang | |
| 2005/0038328 A1 | 2/2005 | Stoehrer et al. | |
| 2005/0061079 A1 | 3/2005 | Schulman | |
| 2005/0102026 A1 | 5/2005 | Turner et al. | |
| 2005/0131383 A1* | 6/2005 | Chen et al. | 604/502 |
| 2005/0159789 A1 | 7/2005 | Brockway et al. | |
| 2005/0165317 A1 | 7/2005 | Turner et al. | |
| 2005/0182330 A1 | 8/2005 | Brockway et al. | |
| 2005/0187482 A1 | 8/2005 | O'Brien et al. | |
| 2005/0187488 A1 | 8/2005 | Wolf | |
| 2005/0192642 A1 | 9/2005 | Forsell | |
| 2005/0240155 A1 | 10/2005 | Conlon | |
| 2005/0240156 A1 | 10/2005 | Conlon | |
| 2005/0250979 A1 | 11/2005 | Coe | |
| 2005/0267406 A1 | 12/2005 | Hassler | |
| 2005/0267500 A1 | 12/2005 | Hassler et al. | |
| 2005/0272968 A1 | 12/2005 | Byrum et al. | |
| 2005/0277960 A1 | 12/2005 | Hassler et al. | |
| 2005/0277974 A1 | 12/2005 | Hassler et al. | |
| 2005/0283119 A1* | 12/2005 | Uth et al. | 604/175 |
| 2005/0288604 A1 | 12/2005 | Eigler et al. | |
| 2005/0288720 A1 | 12/2005 | Ross et al. | |
| 2005/0288721 A1 | 12/2005 | Girouard et al. | |
| 2005/0288739 A1 | 12/2005 | Hassler et al. | |
| 2005/0288740 A1 | 12/2005 | Hassler et al. | |
| 2005/0288741 A1 | 12/2005 | Hassler et al. | |
| 2005/0288742 A1 | 12/2005 | Giordano et al. | |
| 2006/0002035 A1 | 1/2006 | Gao et al. | |
| 2006/0010090 A1 | 1/2006 | Brockway et al. | |
| 2006/0020224 A1 | 1/2006 | Geiger | |
| 2006/0020305 A1 | 1/2006 | Desai et al. | |
| 2006/0035446 A1 | 2/2006 | Chang et al. | |
| 2006/0047205 A1 | 3/2006 | Ludomirsky et al. | |
| 2006/0049714 A1 | 3/2006 | Liu et al. | |
| 2006/0058627 A1 | 3/2006 | Flaherty et al. | |
| 2006/0064134 A1 | 3/2006 | Mazar et al. | |
| 2006/0085051 A1 | 4/2006 | Fritsch | |
| 2006/0089571 A1 | 4/2006 | Gertner | |
| 2006/0094966 A1 | 5/2006 | Brockway et al. | |
| 2006/0100531 A1 | 5/2006 | Moser | |
| 2006/0113187 A1 | 6/2006 | Deng et al. | |
| 2006/0122285 A1 | 6/2006 | Falloon et al. | |
| 2006/0122863 A1 | 6/2006 | Gottesman et al. | |
| 2006/0142635 A1 | 6/2006 | Forsell | |
| 2006/0149124 A1 | 7/2006 | Forsell | |
| 2006/0149324 A1 | 7/2006 | Mann et al. | |
| 2006/0149327 A1 | 7/2006 | Hedberg et al. | |
| 2006/0157701 A1 | 7/2006 | Bauer et al. | |
| 2006/0161186 A1 | 7/2006 | Hassler et al. | |
| 2006/0178617 A1 | 8/2006 | Adams et al. | |
| 2006/0178695 A1 | 8/2006 | Decant et al. | |
| 2006/0183967 A1 | 8/2006 | Lechner | |
| 2006/0184206 A1 | 8/2006 | Baker et al. | |
| 2006/0189887 A1 | 8/2006 | Hassler et al. | |
| 2006/0189888 A1 | 8/2006 | Hassler et al. | |
| 2006/0189889 A1 | 8/2006 | Gertner | |
| 2006/0199997 A1 | 9/2006 | Hassler et al. | |
| 2006/0211912 A1 | 9/2006 | Dlugos et al. | |
| 2006/0211913 A1 | 9/2006 | Dlugos et al. | |
| 2006/0211914 A1 | 9/2006 | Hassler et al. | |
| 2006/0217668 A1 | 9/2006 | Schulze et al. | |
| 2006/0217673 A1 | 9/2006 | Schulze et al. | |
| 2006/0235310 A1 | 10/2006 | O'Brien et al. | |
| 2006/0235439 A1 | 10/2006 | Molitor et al. | |
| 2006/0235448 A1 | 10/2006 | Roslin et al. | |
| 2006/0244914 A1 | 11/2006 | Cech et al. | |
| 2006/0247682 A1 | 11/2006 | Gerber et al. | |
| 2006/0247719 A1 | 11/2006 | Maschino et al. | |
| 2006/0247722 A1 | 11/2006 | Maschino et al. | |
| 2006/0247723 A1 | 11/2006 | Gerber et al. | |
| 2006/0247724 A1 | 11/2006 | Gerber et al. | |
| 2006/0247725 A1 | 11/2006 | Gerber et al. | |
| 2006/0252982 A1 | 11/2006 | Hassler et al. | |
| 2006/0293625 A1 | 12/2006 | Hunt et al. | |
| 2006/0293626 A1 | 12/2006 | Byrum et al. | |
| 2006/0293627 A1 | 12/2006 | Byrum et al. | |
| 2007/0010790 A1 | 1/2007 | Byrum et al. | |
| 2007/0027356 A1 | 2/2007 | Ortiz | |
| 2007/0027493 A1 | 2/2007 | Ben-Haim et al. | |
| 2007/0067206 A1 | 3/2007 | Haggerty et al. | |
| 2007/0070906 A1 | 3/2007 | Thakur | |
| 2007/0072452 A1 | 3/2007 | Inagaki et al. | |
| 2007/0081304 A1 | 4/2007 | Takeguchi | |
| 2007/0149947 A1 | 6/2007 | Byrum | |
| 2007/0156013 A1 | 7/2007 | Birk | |
| 2007/0167672 A1 | 7/2007 | Dlugos et al. | |
| 2007/0173881 A1 | 7/2007 | Birk et al. | |
| 2007/0179583 A1 | 8/2007 | Goetzinger et al. | |
| 2007/0208313 A1 | 9/2007 | Conlon et al. | |
| 2007/0225781 A1 | 9/2007 | Saadat et al. | |
| 2008/0009680 A1 | 1/2008 | Hassler | |

FOREIGN PATENT DOCUMENTS

| CA | 1119469 | 3/1982 |
|---|---|---|
| CA | 1275135 | 10/1990 |

| | | |
|---|---|---|
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-014487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226611 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |
| WO | 2007142503 A1 | 12/2007 |

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED-6A1EC1B7AE7A&id=HA0E380D3-C27B-9EBF-AAC8-9FAF8851256D&sel=1&sel4=1; 1 page.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB1C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

* cited by examiner

REORIENTATION PORT

FIELD

The present application relates to methods and devices for reorienting a port implanted under the skin.

BACKGROUND

Obesity is a growing global concern, as the number of individuals classified as overweight, obese, or morbidly obese continues to increase every year. Obesity is associated with several co-morbidities, including hypertension, type II diabetes, and sleep apnea. Morbid obesity, defined as when a person is 100 pounds or more over ideal body weight or having a body mass index (BMI) of 40 or greater, poses the greatest risks for severe health problems. Accordingly, a great deal of attention is being focused on treating patients with this condition. One method of treating morbid obesity is the placement of a restriction device, such as an elongated band, around the upper portion of the stomach. Gastric bands are typically comprised of a fluid-filled elastomeric balloon with fixed endpoints that encircles the stomach just inferior to the esophageal-gastric junction. This forms a small gastric pouch above the band and a reduced stoma opening inferior to the gastro-esophageal junction in the stomach. When fluid is infused into the balloon, the band expands against the stomach creating further food intake restriction or a smaller stoma opening in the stomach. To decrease this restriction level, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. Another method for limiting the available food volume in the stomach cavity is implanting an inflatable elastomeric balloon within the stomach cavity itself. The balloon is filled with a fluid to expand against the stomach walls and, thereby, decrease the available food volume within the stomach.

With each of the above-described food limitation devices, safe, effective treatment requires that the device be regularly monitored and adjusted to vary the degree of affect on food intake. With banding devices, the gastric pouch above the band may substantially increase in size following the initial implantation. Accordingly, the stoma opening in the stomach must initially be made large enough to enable the patient to receive adequate nutrition while the stomach adapts to the banding device. As the patient's body adapts to the implant, the band may be adjusted to vary the stoma size. In addition, it is desirable to vary the stoma size in order to accommodate changes in the patient's body or treatment regime, or in a more urgent case, to relieve an obstruction or severe esophageal dysmotility or dilatation. Traditionally, adjusting a hydraulic gastric band required a scheduled clinician visit during which a Huber (non-coring) hypodermic needle and syringe were used to penetrate the patient's skin and add or remove fluid from the balloon. More recently, devices have been developed which enable non-invasive adjustments of the band. An external programmer communicates with the implant using telemetry to control the stoma diameter of the band. During a scheduled visit, a physician places a handheld portion of the programmer near the implant and transmits power and command signals to the implant. The implant in turn adjusts the stoma diameter of the band and transmits a response command to the programmer.

During these gastric band adjustments, it has been difficult to determine how the adjustment is proceeding, and whether an adjustment will have its intended effect. In an attempt to determine the efficacy of an adjustment, some physicians have used fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructed at that time, and does not provide any information about the efficacy of the adjustment or the impact of the adjustment the following day as the patient begins to consume more solid foods. Oftentimes, physicians may simply adopt an experimental method based upon their prior experience, and the results of an adjustment may not be discovered until hours or days later, when the patient experiences a complete obstruction of the stomach cavity.

Another problem that can arise is the ability to handle a port, such as a fluid port, used to fluidically communicate with the gastric band to increase or decrease the restriction the band provides. For example, in order to introduce additional fluid to increase the restriction of the gastric band, a Huber needle must be inserted through the skin and into the port septum. This can be difficult as the stomach anatomy is not a flat surface and the port may be angled, the port may shift locations beneath the skin, or the port can flip over entirely.

Accordingly, there remains a need for improved methods and devices for reorienting a port implanted under the skin.

SUMMARY

Various methods and device for reorienting a port are provided. In one embodiment, an implantable port is provided and includes a base adapted to be anchored to tissue, and a housing pivotally mounted on the base and having a septum formed therein and adapted to receive fluid and to provide access to a fluid reservoir formed within the housing. In an exemplary embodiment, the housing can be pivotally mounted to the base using a ball and socket joint. For example, at least one of a distal surface of the housing and a proximal surface of the base can be convex, and the other one of the distal surface of the housing and the proximal surface of the base can be concave. The implantable port can also optionally be adapted to be anchored to tissue. For example, the base can include one or more suture-receiving members adapted to receive a suture for anchoring the base to tissue, or the base can include one or more anchors adapted to be deployed into tissue. The implantable port can also include additional features, such as the housing having a magnetic portion adapted to align the housing with an external magnet.

In another embodiment, an implantable port can include a base adapted to be anchored to tissue, and a housing pivotally mounted on the base. The housing can have a septum formed therein and adapted to receive fluid and to provide access to a fluid reservoir formed within the housing. A magnetic member can be coupled to the housing and it can be adapted to align the housing with an external magnet. The magnetic portion can be disposed around an opening in the housing having the septum.

A gastric restriction system is also provided, and in one embodiment includes an implantable gastric restriction device configured to form a restriction in a patient, and an implantable port in fluid communication with the implantable gastric restriction device. The implantable port can be configured to receive fluid from a fluid source external to the patient. For example, a septum can be formed in a housing of the port and it can be adapted to receive fluid and to provide access to a fluid reservoir formed within the housing. The implantable port also includes a base adapted to anchor to tissue. The housing can be pivotally coupled to the base. In one exemplary embodiment, the housing is pivotally coupled to the base using a ball and socket joint. For example, at least one of a distal surface of the housing and a proximal surface of the base can be convex, and the other one of the distal surface of the housing and the proximal surface of the base can be concave. The port can also include other features, such as a magnetic portion located within the housing. A catheter can also be included and it can extend between the gastric restriction device and the implantable port for delivering fluid from the fluid reservoir of the housing to the gastric restriction device to adjust an amount of restriction applied by the gastric restriction device.

Methods for accessing a port implanted in tissue are also provided, and in one embodiment the method can include pivoting a housing disposed beneath a skin surface and movably coupled to a base anchored in tissue, for example, to the fascia, to position a septum formed on the housing in a desired position. In an exemplary embodiment, the method can also include inserting a needle into the septum formed in the housing, and injecting fluid into the housing. The fluid is delivered from the housing to a gastric restriction device coupled to the housing. In another embodiment, pivoting the housing can be done by attracting a magnetic portion of the housing with a magnet positioned adjacent the skin surface so as to align the housing with a needle being inserted into the septum.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
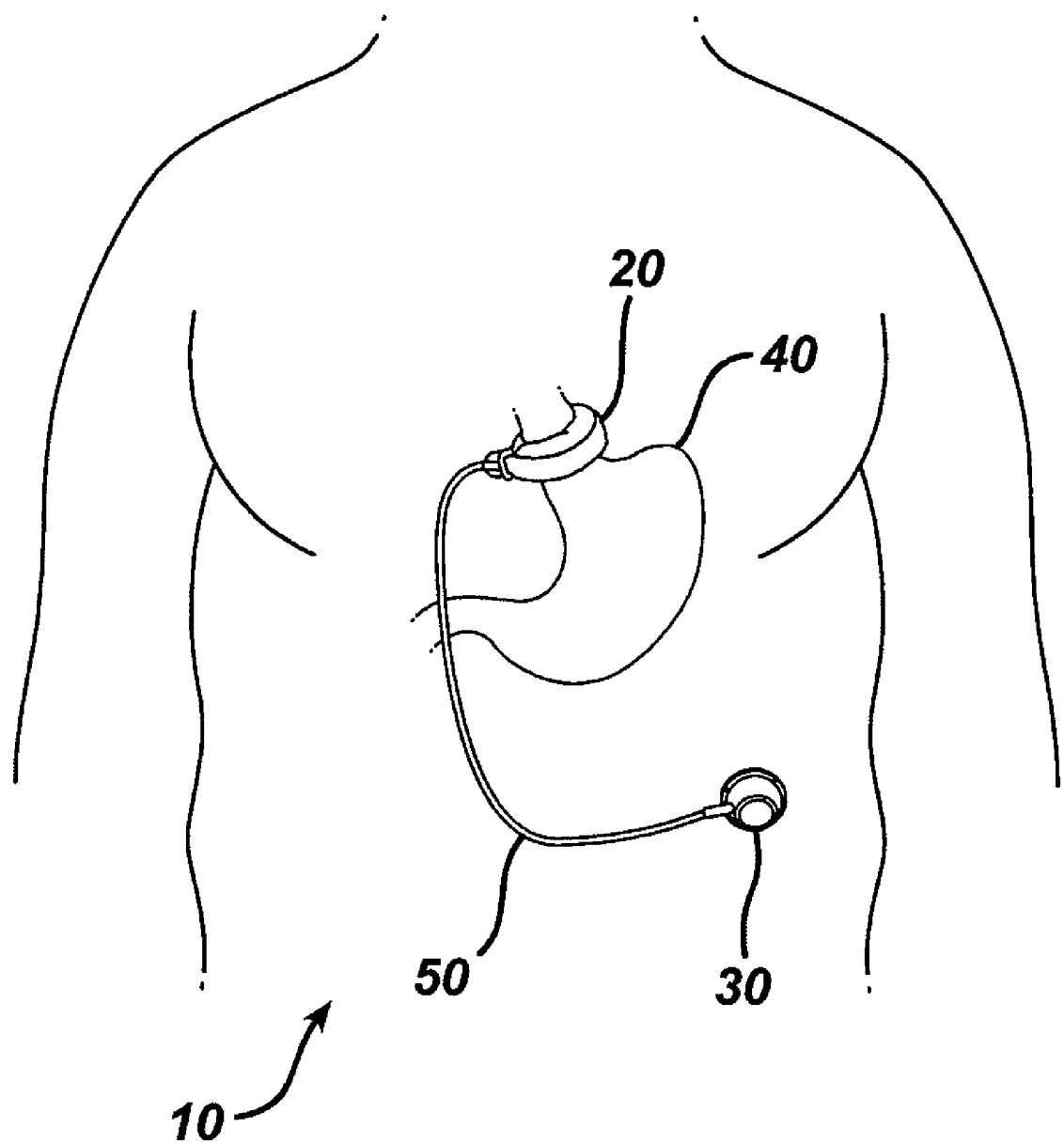
FIG. 1 is a schematic diagram of one embodiment of a restriction system.

While the present invention can be used with a variety of restriction systems known in the art, FIG. 1 illustrates one exemplary embodiment of a food intake restriction system 10. As shown, the system 10 generally includes an adjustable gastric band 20 that is configured to be positioned around the upper portion of a patient's stomach 40, and an injection port 30 that is fluidly coupled to the adjustable gastric band 20, e.g., via a catheter 50. The injection port 30 is adapted to allow fluid to be introduced into and removed from the gastric band 20 to thereby adjust the size of the band, and thus the pressure applied to the stomach. The injection port 30 can thus be implanted at a location within the body that is accessible through the tissue. Typically, injection ports are positioned in the lateral subcostal region of the patient's abdomen under the skin and layers of fatty tissue. Surgeons also typically implant injection ports on the sternum of the patient.

Figure 2A:
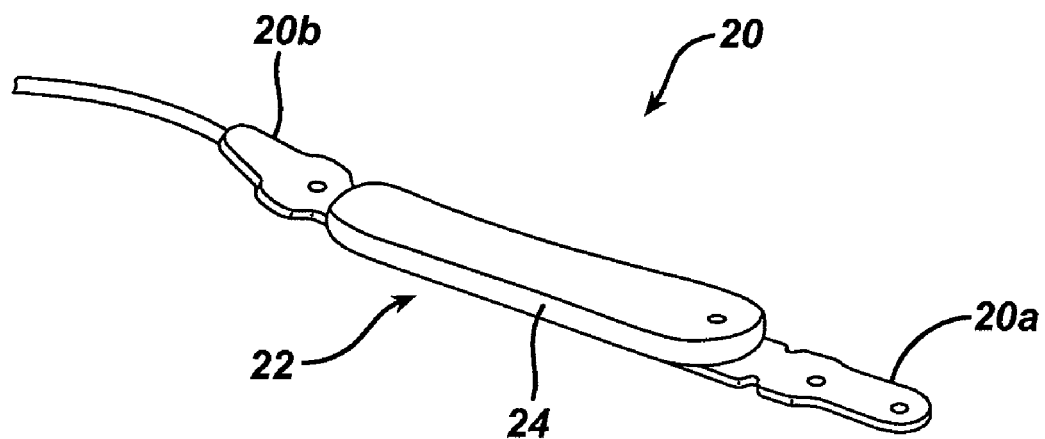
FIG. 2A is a perspective view of a restriction device of the restriction system of FIG. 1.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be secured to each other. Various mating techniques can be used to secure the ends 20a, 20b to one another. In the illustrated embodiment, the ends 20a, 20b are in the form of straps that mate together, with one laying on top of the other. The gastric band 20 can also include a variable volume member, such as an inflatable balloon 24, that is disposed or formed on one side of the support structure 22, and that is configured to be positioned adjacent to tissue. The balloon 24 can expand or contract against the outer wall of the stomach to form an adjustable stoma for controllably restricting food intake into the stomach. A person skilled in the art will appreciate that the gastric band can have a variety of other configurations, moreover the various methods and devices disclosed herein have equally applicability to other types of implantable bands. For example, bands are used for the treatment of fecal incontinence, as described in U.S. Pat. No. 6,461,292 which is hereby incorporated herein by reference. Bands can also be used to treat urinary incontinence, as described in U.S. Patent Application 2003/0105385 which is hereby incorporated herein by reference. Bands can also be used to treat heartburn and/or acid reflux, as disclosed in U.S. Pat. No. 6,470,892 which is hereby incorporated herein by reference. Bands can also be used to treat impotence, as described in U.S. Patent Application 2003/0114729 which is hereby incorporated herein by reference.

Figure 2B:
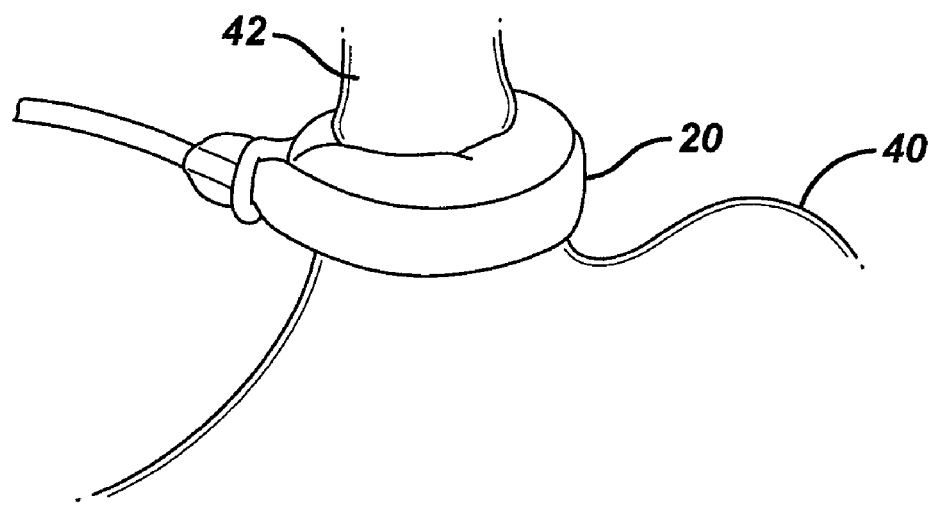
FIG. 2B is a perspective view of the restriction device of FIG. 2A applied about the gastro-esophageal junction of a stomach.

FIG. 2B shows the adjustable gastric band 20 applied about the gastro-esophageal junction of a patient. As shown, the band 20 at least substantially encloses the upper portion of the stomach 40 near the junction with the esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band.

As indicated above, the system also includes an injection port 30 for receiving and delivering fluid to the gastric band 20. The present invention is particularly directed towards methods and devices for reorienting an implantable port, such as injection port 30. In one exemplary embodiment, the implantable port can have a base adapted to be anchored to tissue, and a housing pivotally mounted on the base and having a septum formed therein and adapted to receive fluid and to provide access to a fluid reservoir formed within the housing. The base and the housing of the port can be pivotally coupled to one another to allow for reorientation of the port after the port is implanted under the surface of the skin into tissue. Since ports tend to shift once implanted, the ability to reorient the port to provide fluid access is particularly advantageous.

Figure 3:
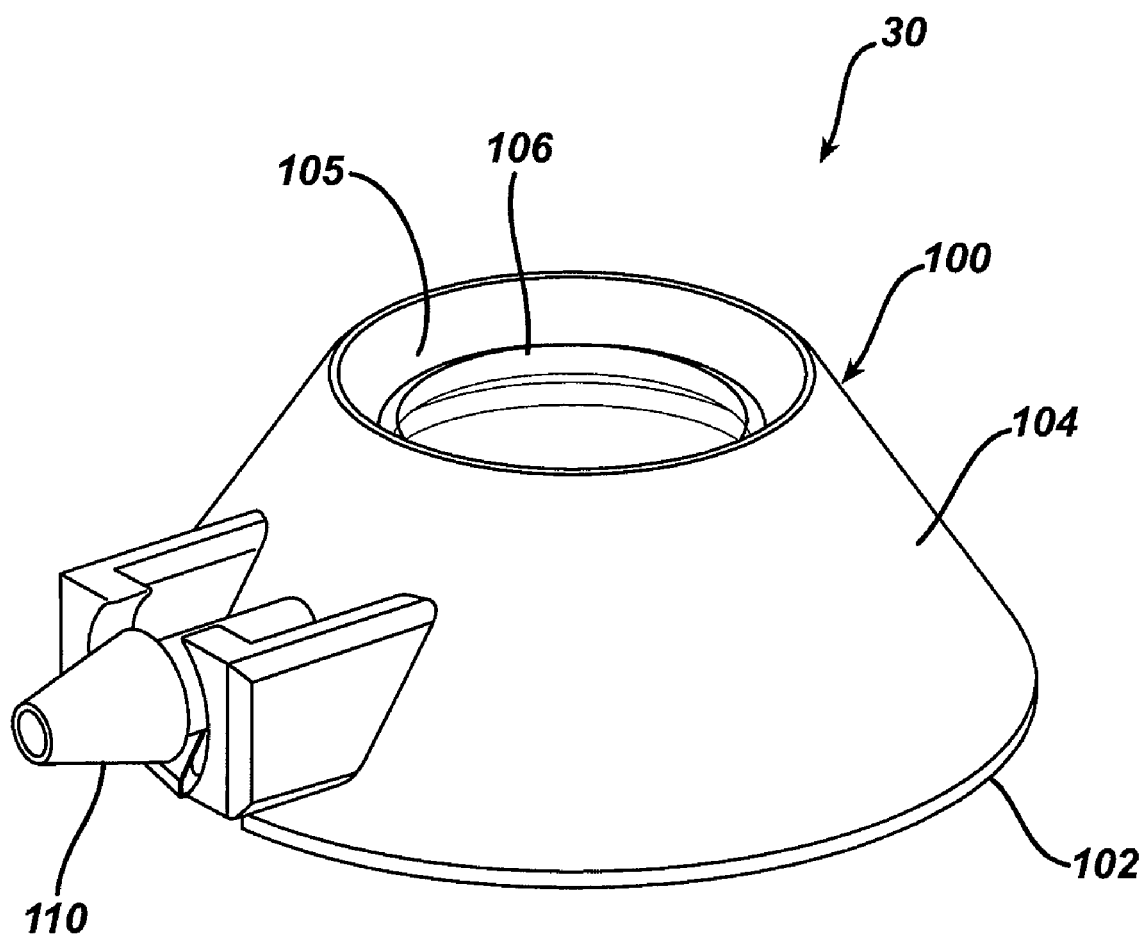
FIG. 3 is a perspective view of one embodiment of an injection port of the restriction system of FIG. 1.
Figure 4:
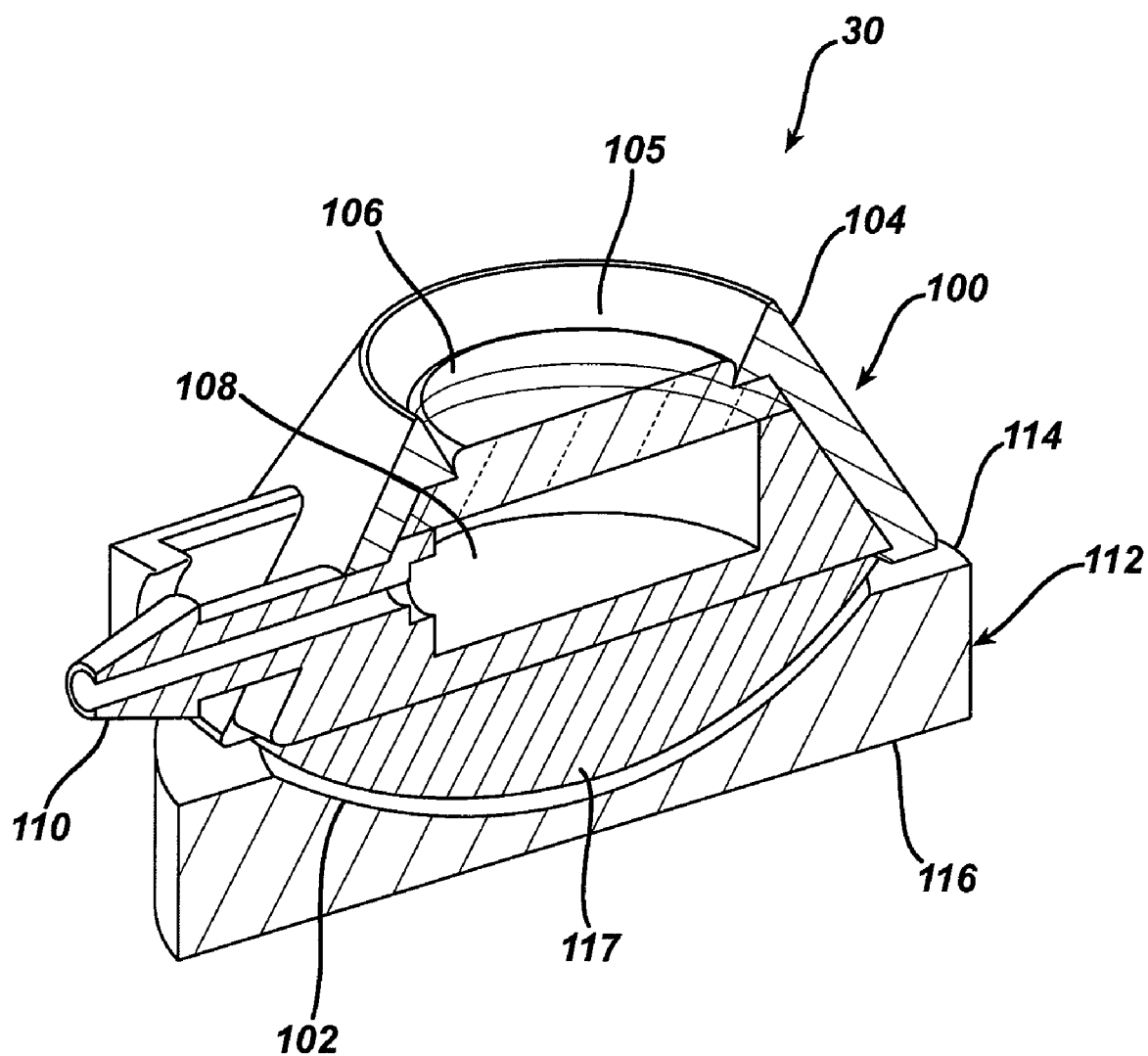
FIG. 4 is a cross-sectional perspective view of the injection port of FIG. 3.

FIGS. 3 and 4 illustrate the injection port 30 in more detail. As shown, the port 30 has a generally conical housing 100 with a distal or bottom surface 102 and a perimeter wall 104 extending proximally from the bottom surface 102 and defining a proximal opening 105. A person skilled in the art will appreciate that the housing 100 can have any shape and size but it is preferably adapted to be implanted in tissue. The proximal opening 105 can include a needle-penetrable septum 106 extending there across and providing access to a fluid reservoir 108 formed within the housing 100. The septum 106 is preferably placed in a proximal enough position such that the depth of the reservoir 108 is sufficient enough to expose the open tip of a needle, such as a Huber needle, so that fluid transfer can take place. The septum 106 can be arranged so that it will self seal after being punctured by a needle and the needle is withdrawn. As further shown in FIGS. 3 and 4, the port 30 can further include a catheter tube connection member 110 that is in fluid communication with the reservoir 108 and that is configured to couple to a catheter, such as the catheter 50 shown in FIG. 1. A person skilled in the art will appreciate that the housing 100 can be made from any number of materials, including stainless steel, titanium, or polymeric materials, and the septum can likewise be made from any number of materials, including silicone.

Figure 8:
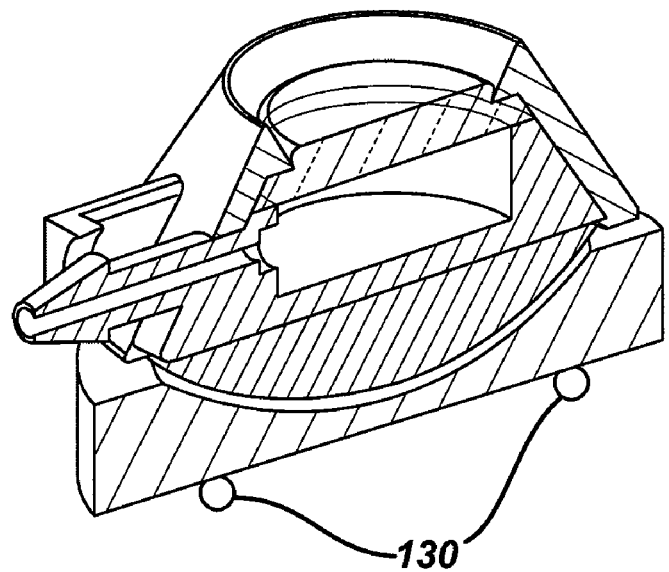
FIG. 8 is a perspective view of one embodiment of an injection port of the restriction system of FIG. 1 having one or more suture-receiving members adapted to receive a suture for anchoring a base of the port to tissue.
Figure 9:
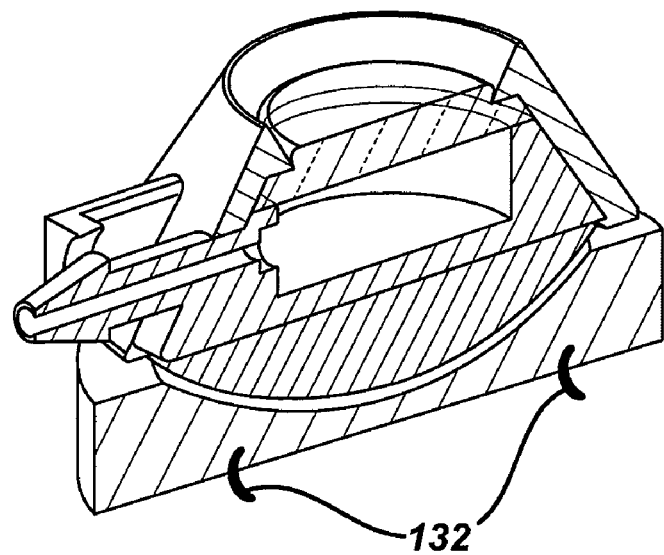
FIG. 9 is a perspective view of another embodiment of an injection port of the restriction system of FIG. 1 having one or more anchors adapted to be deployed into tissue to anchor a base of the port thereto.

The port 30 can further include a base 112 having a proximal surface 114 that is adapted to couple to the housing 100 and a distal surface 116 that is adapted to rest on and/or anchor to tissue. The distal surface 116 of the base 112 can be anchored to tissue in a variety of ways. For example, the base 112 can include one or more suture-receiving members 130 adapted to receive a suture for anchoring the base 112 to tissue, shown in FIG. 8, or the base 112 can include one or more anchors 132 adapted to be deployed into tissue, shown in FIG. 9. A person skilled in the art will appreciate that the any technique can be used to anchor the base 112 of the port 30 in tissue. Moreover, a person skilled in the art will appreciate that the anchoring techniques shown in FIGS. 8 and 9 can be used with any of the embodiments of the invention described herein.

Figure 5:
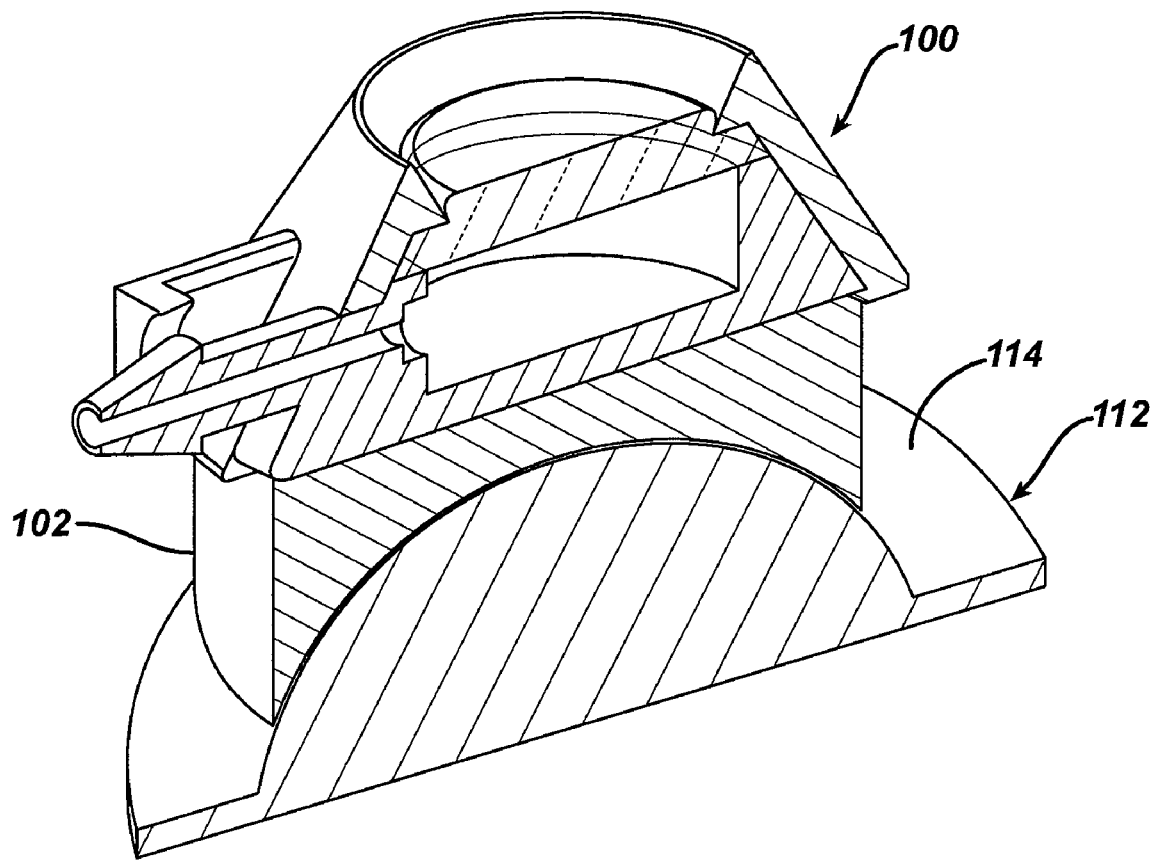
FIG. 5 is a cross-sectional perspective view of another embodiment of an injection port of FIG. 1.

In order to facilitate reorientation of the port 30, the distal surface 102 of the housing 100 and the proximal surface 114 of the base 112 can be configured to move relative to one another. In one exemplary embodiment, the distal surface 102 of the housing and the proximal surface 114 of the base 112 are adapted to pivot relative to one another, for example, using a ball and socket configuration. In one embodiment, shown in FIG. 4, the distal surface 102 of the housing 100 is convex and is adapted to be received within a corresponding concave surface or cavity 117 formed in the proximal surface 114 of the base 112. This allows the housing 100 to pivot relative to the base 112 to reorient the housing 100 when the base 112 is positioned on and/or anchored in tissue. In another embodiment, shown in FIG. 5, the distal surface 102 of the housing 100 can include a concave cavity and it can be adapted to receive a corresponding convex surface formed on the proximal surface 114 of the base 112. A person skilled in the art will appreciate that any configuration of the housing 100 and the base 112 can be used as long as the housing 100 and the base 112 can move relative to one another to allow reorientation of the port.

In use, the port 30 can be implanted under the skin and the base 112 of the port 30 can be positioned on and/or anchored to tissue. For example, the port 30 can be implanted just beneath the tissue surface to allow a needle or other device to be penetrated through tissue and into the port 30 to add or remove fluid from the restriction system 10. In certain exemplary embodiments, the port 30 can be implanted in the fascia. After implantation, reorientation of the port 30 may be necessary as the port can shift or flip under the skin and access to the septum 106 of the housing 100 may be limited. The port 30 can be reoriented in variety of ways. For example, the port 30 can be manually manipulated through the skin to pivot the housing 100 relative to the base 112, thus allowing a needle to be passed through the skin and into the septum 106 in order to deliver fluid to the fluid reservoir 108 located within the housing 100.

Figure 6:
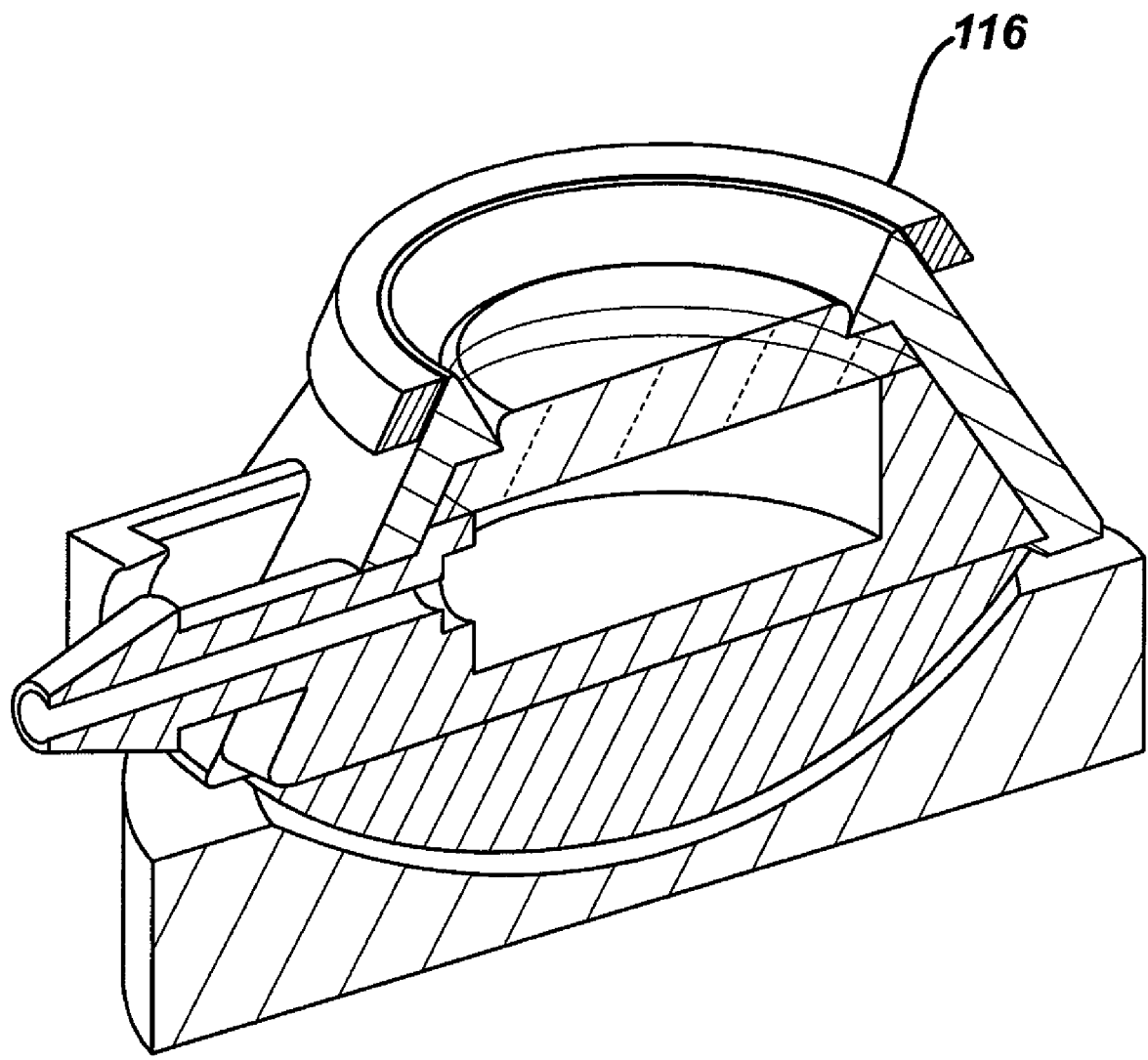
FIG. 6 is a perspective view of yet another embodiment of an injection port of FIG. 1 having a magnetic member coupled thereto for facilitating reorientation of the port.

In another embodiment, the injection port 30 can include a magnetic member 116 coupled thereto for facilitating reorientation of the port 30. The magnetic member 116 can have a variety of configurations. For example, the magnetic member 116 can be in the form of a cylindrical magnet with an opening therethrough. The opening can be sized and shaped to extend around a portion of the port 30. In one embodiment, shown in FIG. 6, the magnetic member 116 is configured to be disposed around a proximal portion of the housing 100. A person skilled in the art will appreciate, however, that the magnetic member 116 can have any configuration and can be disposed at any location that allows the magnetic member 116 to be used for reorienting the port 30. The magnetic member 116 can also be coupled to the port 30 in a variety of ways. For example, the magnetic member 116 can be unitary with the port 30 or they can be separate components and the magnetic member 116 can be fixedly or removably coupled to the port 30. In addition, the magnetic member 116 can be formed from a single magnet, as shown in FIG. 6, or it can be formed from a plurality of magnets coupled to the port 30 in any configuration. For example, if the magnetic member 116 is formed from a plurality of magnets, the magnets can be coupled to the housing 100 of the port 30 and spaced radially around a proximal portion of the housing 100.

Figure 7:
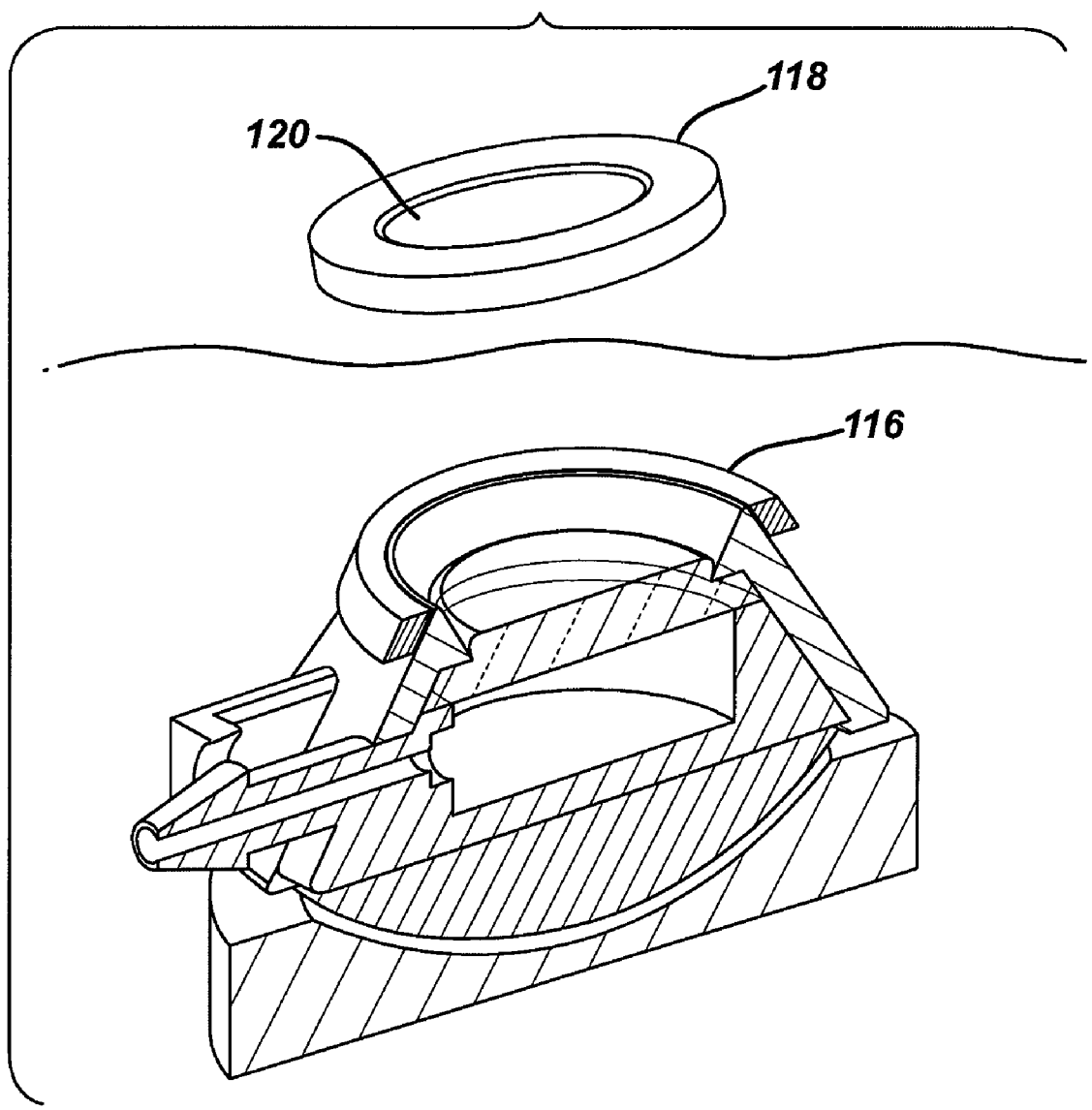
FIG. 7 is a perspective view of the injection port of FIG. 6 showing an external magnet that can be used to apply a force to the magnetic member to reorient the port.

To facilitate reorientation of the port 30, the magnet member 116 can be used in conjunction with an external magnet 118 that is placed against a skin surface. The external magnet 118 can be used to apply a force to the magnetic member 116 coupled to the housing 100 of the port 30 to align the external magnet 118 and the magnetic member 116. This can cause the housing 100 to pivot relative to the base 112 of the port 30 to reorient the housing 100 so that the septum 106 is directed towards the skin surface. For example, as shown in FIG. 7, the external magnet 118 can be placed over the skin at a location near the implanted injection port 30. The external magnet 118 is positioned in such a way as to cause reorientation of the port 30 to allow a needle to be inserted through the skin and into the septum 106 of the housing 100. In order to facilitate insertion of the needle into the septum 106, the external magnet 118 can include an opening 120 therethrough to allow the needle to pass through the opening 120, through the skin, and into the septum 106 of the port 30 while the magnet force maintains alignment between the external magnet 118 and the magnetic member 116.

The reorientation techniques described above can be used with any restriction system, and can be applied to various types of ports.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of accessing a port implanted in tissue, comprising:
   pivoting a housing disposed beneath a skin surface and movably coupled to a base anchored in tissue to change an angular orientation of a central longitudinal axis of a septum formed on the housing relative to a central longitudinal axis of the base.

2. The method of claim 1, further comprising inserting a needle into the septum formed in the housing, and injecting fluid into the housing.

3. The method of claim 2, wherein the fluid is delivered from the housing to a gastric restriction device coupled to the housing.

4. The method of claim 1, wherein the base of the port is anchored to fascia.

5. The method of claim 1, further comprising aligning the housing by attracting a magnetic portion on the housing with a magnet positioned adjacent the skin surface so as to align the housing with a needle being inserted into the septum.

6. The method of claim 1, wherein the base is anchored in tissue prior to pivoting the housing.

7. The method of claim 1, wherein the housing is manually manipulated to pivot the housing relative to the base.

8. A method of accessing a port implanted in tissue, comprising:
   positioning a magnet adjacent to a skin surface, the magnet attracting a magnetic portion of a housing disposed beneath the skin surface and movably coupled to a base anchored to tissue to change an angular orientation of a central longitudinal axis of a septum formed on the housing relative to a central longitudinal axis of the base.

9. The method of claim 8, further comprising inserting a needle into the septum formed in the housing, and injecting fluid into the housing.

10. The method of claim 9, wherein the needle is inserted through an opening formed in the magnet and through the septum to inject fluid into the housing.

* * * * *